US012708637B2

(12) United States Patent
Padler-Karavani et al.

(10) Patent No.: US 12,708,637 B2
(45) Date of Patent: Aug. 18, 2026

(54) IMMUNOGENIC COMPOSITIONS CONTAINING N-GLYCOLYLNEURAMINIC ACID BEARING NANOPARTICLES

(71) Applicant: RAMOT AT TEL-AVIV UNIVERSITY LTD., Tel Aviv (IL)

(72) Inventors: Vered Padler-Karavani, Tel Aviv (IL); Eliran Moshe Reuven, Tel Aviv (IL); Shani Leviatan Ben-Arye, Tel Aviv (IL)

(73) Assignee: RAMOT AT TEL-AVIV UNIVERSITY LTD., Tel Aviv (IL)

( * ) Notice: Subject to any disclaimer, the term of this patent is extended or adjusted under 35 U.S.C. 154(b) by 1382 days.

(21) Appl. No.: 17/296,504

(22) PCT Filed: Nov. 21, 2019

(86) PCT No.: PCT/IL2019/051271

§ 371 (c)(1),
(2) Date: May 24, 2021

(87) PCT Pub. No.: WO2020/105048

PCT Pub. Date: May 28, 2020

(65) Prior Publication Data

US 2022/0031720 A1 Feb. 3, 2022

Related U.S. Application Data

(60) Provisional application No. 62/770,749, filed on Nov. 22, 2018.

(51) Int. Cl.

| | |
|---|---|
| ***A61K 31/7012*** | (2006.01) |
| ***A61K 9/127*** | (2006.01) |
| ***A61K 39/00*** | (2006.01) |
| ***A61K 39/39*** | (2006.01) |
| ***A61K 39/395*** | (2006.01) |
| ***A61P 35/00*** | (2006.01) |

(52) U.S. Cl.

CPC .......... *A61K 31/7012* (2013.01); *A61K 9/127* (2013.01); *A61K 39/0011* (2013.01); *A61K 39/001169* (2018.08); *A61K 39/001171* (2018.08); *A61K 39/39* (2013.01); *A61K 39/3955* (2013.01); *A61P 35/00* (2018.01)

(58) Field of Classification Search

CPC .................................................. A61K 31/7012

See application file for complete search history.

(56) References Cited

U.S. PATENT DOCUMENTS

| | | | |
|---|---|---|---|
| 6,149,921 | A | 11/2000 | Rodriguez |
| 8,591,917 | B2 | 11/2013 | Molina |
| 9,423,401 | B2 | 8/2016 | Varki |
| 10,052,370 | B2 | 8/2018 | Savelyeva |
| 2006/0099145 | A1 | 5/2006 | Takeyama |

FOREIGN PATENT DOCUMENTS

| | | | |
|---|---|---|---|
| WO | 2013052167 | A2 | 4/2013 |
| WO | 2014194053 | A2 | 12/2014 |
| WO | 2017004579 | A1 | 1/2017 |
| WO | 2018049304 | A1 | 3/2018 |
| WO | 2018217588 | A1 | 11/2018 |

OTHER PUBLICATIONS

Segatori, V. I., et al., 2012, Antitumor protection by NGcGM3/VSSP vaccine against transfected B16 mouse melanoma cells overexpressing N-glycolylated gangliosides, In Vivo, 26:609-618.*
Gyorgy, B., et al., 2011, Membrane vesicles, current state-of-the-art: emerging role of extracellular vesicles, Cell. Mol. Life Sci. 68: 2667-2688.*
Srivatsav, A. T., and S. Kapoor, Apr. 2021, The Emerging World of Membrane Vesicles: Functional Relevance, Tharanostic Avenues and Tools for Investigating Membrane Function, Front. Mol. Biosci. 8, Article 640355, pp. 1-24.*
Zeng, H., Jul. 2022, What is a cell type and how to define it? Cell 185:2739-2755.*
Estevez et al., (2000) Enhancement of the immune response to poorly immunogenic gangliosides after incorporation into very small size proteoliposomes (VSSP). Vaccine 18(1-2): 190-197.
Mazorra et al., (2008) Immunization with a GM3 ganglioside nanoparticulated vaccine confers an effector CD8(+) T cells-mediated protection against melanoma B16 challenge. Cancer Immunol Immunother 57(12): 1771-1780.
Wang et al., (2014) Erythrocytes from GGTA1/CMAH knockout pigs: implications for xenotransfusion and testing in non-human primates. Xenotransplantation. Author manuscript; available in PMC Jul. 2, 2015. Published in final edited form as: Xenotransplantation. Jul.-Aug. 2014; 21(4): 376-384.
Padler-Karavani et al., (2019) Active cancer vaccine targeting carbohydrates for immunotherapy. J Immunol May 1, 2019, 202 (1 Supplement) 70.14. Retrieved from: https://www.jimmunol.org/content/202/1_Supplement/70.14 on Jun. 14, 2022.
Okerblom and Varki (2017) Biochemical, Cellular, Physiological, and Pathological Consequences of Human Loss of N-Glycolylneuraminic Acid. Chembiochem 18(13): 1155-1171.
Ott et al., (2017) An immunogenic personal neoantigen vaccine for patients with melanoma. Nature. Author manuscript; available in PMC Jan. 13, 2018. Published in final edited form as: Nature. Jul. 13, 2017; 547(7662): 217-221. 34 pages. With corrigendum.

(Continued)

*Primary Examiner* — Jeffrey S Parkin
(74) *Attorney, Agent, or Firm* — Ballard Spahr LLP

(57) ABSTRACT

The present invention provides an active cancer vaccine and specifically an immunogenic compositions of membrane vesicles that serve as biomimetic nanoparticles derived from eukaryotic cell membranes that bear N-glycolylneuraminic acid glycoconjugates. These compositions can elicit beneficial immunological responses for treatment of Neu5Gc-positive tumors. The present invention provides methods of generating and using Neu5Gc-conjugated nanoparticles from eukaryotic cells membranes designated nano-ghosts.

12 Claims, 13 Drawing Sheets

(56) References Cited

OTHER PUBLICATIONS

Ott et al., (2017) Combination immunotherapy: a road map. J Immunother Cancer 5: 16; 15 pages.
Padler-Karavani (2014) Aiming at the sweet side of cancer: aberrant glycosylation as possible target for personalized-medicine. Cancer Lett 352(1): 102-112.
Padler-Karavani (2016) Glycan Microarray Reveal the Sweet Side of Cancer Vaccines. Cell Chem Biol 23(12): 1446-1447.
Padler-Karavani et al., (2008) Cross-comparison of protein recognition of sialic acid diversity on two novel sialoglycan microarrays. J Biol Chem 287(27): 22593-22608.
Padler-Karavani et al., (2008) Diversity in specificity, abundance, and composition of anti-Neu5Gc antibodies in normal humans: potential implications for disease. Glycobiology 18(10): 818-830.
Padler-Karavani et al., (2011) Human xeno-autoantibodies against a non-human sialic acid serve as novel serum biomarkers and immunotherapeutics in cancer. Cancer Res 71(9): 3352-3363.
Pappalardo et al., (2010) Vaccine protocols optimization: in silico experiences. Biotechnol Adv 28(1): 82-93.
Pardoll and Allison (2004) Cancer immunotherapy: breaking the barriers to harvest the crop. Nat Med 10(9): 887-892.
Pearce et al., (2014) Hormesis in cancer immunology: Does the quantity of an immune reactant matter? Oncoimmunology 3: e29312; 4 pages.
Pearce et al., (2014) Inverse hormesis of cancer growth mediated by narrow ranges of tumor-directed antibodies. Proc Natl Acad Sci U S A 111(16): 5998-6003.
Pham et al., (2009) Evidence for a novel human-specific xeno-auto-antibody response against vascular endothelium. Blood 114(25): 5225-5235.
Poland et al., (2007) Heterogeneity in vaccine immune response: the role of immunogenetics and the emerging field of vaccinomics. Clin Pharmacol Ther 82(6): 653-664.
Ragupathi et al., (2009) Synthesis of sialyl Lewis(a) (sLe (a), CA19-9) and construction of an immunogenic sLe(a) vaccine. Cancer Immunol Immunother. Author manuscript; available in PMC Feb. 25, 2010. Published in final edited form as: Cancer Immunol Immunother. Sep. 2009; 58(9): 1397-1405. 16 pages.
Rajagopal and Harikumar (2018) The Origin and Functions of Exosomes in Cancer. Front Oncol 8: 66; 13 pages.
Rao et al., (2015) Red Blood Cell Membrane as a Biomimetic Nanocoating for Prolonged Circulation Time and Reduced Accelerated Blood Clearance. Small 11(46): 6225-6236.
Restifo et al., (2012) Adoptive immunotherapy for cancer: harnessing the T cell response. Nat Rev Immunol. Author manuscript; available in PMC Dec. 13, 2018. Published in final edited form as: Nat Rev Immunol. Mar. 22, 2012; 12(4): 269-281. 30 pages.
Ribas and Wolchok (2018) Cancer immunotherapy using checkpoint blockade. Science. Author manuscript; available in PMC Jul. 30, 2020. Published in final edited form as: Science. Mar. 23, 2018; 359(6382): 1350-1355. 18 pages.
Rosenberg and Restifo (2015) Adoptive cell transfer as personalized immunotherapy for human cancer. Science 348(6230): 62-68.
Salama et al., (2017) Neu5Gc and α1-3 GAL Xenoantigen Knockout Does Not Affect Glycemia Homeostasis and Insulin Secretion in Pigs. Diabetes 66(4): 987-993.
Samraj et al., (2014) Involvement of a non-human sialic Acid in human cancer. Front Oncol 4: 33; 13 pages.
Samraj et al., (2015) A red meat-derived glycan promotes inflammation and cancer progression. Proc Natl Acad Sci U S A 112(2): 542-547.
Samraj et al., (2018) Polyclonal human antibodies against glycans bearing red meat-derived non-human sialic acid N-glycolylneuraminic acid are stable, reproducible, complex and vary between individuals: Total antibody levels are associated with colorectal cancer risk. PLoS One 13(6): e0197464; 27 pages.
Schunk and Macallum (2005) Applications and optimization of immunization procedures. ILAR J 46(3): 241-257.
Scott et al., (2012) Antibody therapy of cancer. Nat Rev Cancer 12(4): 278-287.
Scott et al., (2012) Monoclonal antibodies in cancer therapy. Cancer Immun 12: 14; 8 pages.
Segatori et al., (2012) Antitumor protection by NGcGM3/VSSP vaccine against transfected B16 mouse melanoma cells overexpressing N-glycolylated gangliosides. In Vivo 26(4): 609-617.
Sharma et al., (2011) Novel cancer immunotherapy agents with survival benefit: recent successes and next steps. Nat Rev Cancer. Author manuscript; available in PMC Aug. 23, 2012. Published in final edited form as: Nat Rev Cancer. Oct. 24, 2011; 11(11): 805-812. 18 pages.
Sharma et al., (2017) Primary, Adaptive, and Acquired Resistance to Cancer Immunotherapy. Cell 168(4): 707-723.
Siegrist CA (2008) Section 1: General aspects of vaccination. Vaccine immunology. In: Vaccines; 5th Edition. Edited by: Plotkin S, Orenstein W, Offit P. Saunders. pp. 17-36.
Son et al., (2016) T/Tn immunotherapy avoiding immune deviation. Int J Immunopathol Pharmacol 29(4): 812-817.
Steck (1974) The organization of proteins in the human red blood cell membrane. A review. J Cell Biol 62(1): 1-19.
Su et al., (2017) Enhanced Blood Suspensibility and Laser-Activated Tumor-specific Drug Release of Theranostic Mesoporous Silica Nanoparticles by Functionalizing with Erythrocyte Membranes. Theranostics 7(3): 523-537. With erratum.
Tangvoranuntakul et al., (2003) Human uptake and incorporation of an immunogenic nonhuman dietary sialic acid. Proc Natl Acad Sci U S A 100(21): 12045-12050.
Terbuch and Lopez (2018) Next Generation Cancer Vaccines—Make It Personal! Vaccines (Basel) 6(3): 52; 17 pages.
Tran et al., (2017) 'Final common pathway' of human cancer immunotherapy: targeting random somatic mutations. Nat Immunol. Author manuscript; available in PMC Dec. 17, 2018. Published in final edited form as: Nat Immunol. Feb. 15, 2017; 18(3): 255-262. 18 pages.
Türeci et al., (2016) Targeting the Heterogeneity of Cancer with Individualized Neoepitope Vaccines. Clin Cancer Res 22(8): 1885-1896.
Villa et al., (2015) Delivery of drugs bound to erythrocytes: new avenues for an old intravascular carrier. Ther Deliv 6(7): 795-826.
Wang and Wang (2017) Immune targets and neoantigens for cancer immunotherapy and precision medicine. Cell Res 27(1): 11-37.
Whiteside et al., (2016) Emerging Opportunities and Challenges in Cancer Immunotherapy. Clin Cancer Res 22(8): 1845-1855.
Ye et al., (2018) Cancer vaccine: learning lessons from immune checkpoint inhibitors. J Cancer 9(2): 263-268.
Zahm et al., (2017) Vaccination with High-Affinity Epitopes Impairs Antitumor Efficacy by Increasing PD-1 Expression on CD8+ T Cells. Cancer Immunol Res 5(8): 630-641.
Zappasodi et al., (2018) Emerging Concepts for Immune Checkpoint Blockade-Based Combination Therapies. Cancer Cell 33(4): 581-598 with erratum.
Zhang et al., (2017) Personalized cancer vaccines: Targeting the cancer mutanome. Vaccine. Author manuscript; available in PMC Feb. 15, 2018. Published in final edited form as: Vaccine. Feb. 15, 2017; 35(7): 1094-1100. 16 pages.
Zheng et al., (2015) Improvement of the immune efficacy of carbohydrate vaccines by chemical modification on the GM3 antigen. Org Biomol Chem 13(22): 6399-6406.
Zimmermann S and Lepenies B (2015) Glycans as Vaccine Antigens and Adjuvants: Immunological Considerations. In: Lepenies B. (eds) Carbohydrate-Based Vaccines. Methods in Molecular Biology, vol. 1331. Humana Press, New York, NY. https://doi.org/10.1007/978-1-4939-2874-3_2. pp. 11-26.
Reuven et al., (2019) Biomimetic Glyconanoparticle Vaccine for Cancer Immunotherapy. ACS Nano 13(3): 2936-2947.
Aldous and Dong (2018) Personalized neoantigen vaccines: A new approach to cancer immunotherapy. Bioorg Med Chem 26(10): 2842-2849.
Allison (2015) Immune Checkpoint Blockade in Cancer Therapy: The 2015 Lasker-DeBakey Clinical Medical Research Award. JAMA 314(11): 1113-1114.
Amon et al., (2014) Glycans in immune recognition and response. Carbohydr Res 389: 115-122.

(56) References Cited

OTHER PUBLICATIONS

Amon et al., (2017) Glycan microarray reveal induced IgGs repertoire shift against a dietary carbohydrate in response to rabbit anti-human thymocyte therapy. Oncotarget 8(68): 112236-112244.
Angata and Varki (2002) Chemical diversity in the sialic acids and related alpha-keto acids: an evolutionary perspective. Chem Rev 102(2): 439-469.
Anish et al., (2014) Chemical biology approaches to designing defined carbohydrate vaccines. Chem Biol 21(1): 38-50.
Antia et al., (2018) Heterogeneity and longevity of antibody memory to viruses and vaccines. PLoS Biol 16(8): e2006601; 15 pages.
Azvolinsky (2013) Cancer vaccines: always a bridesmaid, never a bride? J Natl Cancer Inst 105(4): 248-249.
Bae et al., (2018) Exosomes derived from cancerous and non-cancerous cells regulate the anti-tumor response in the tumor microenvironment. Genes Cancer 9(3-4): 87-100.
Bardor et al., (2005) Mechanism of uptake and incorporation of the non-human sialic acid N-glycolylneuraminic acid into human cells. J Biol Chem 280(6): 4228-4237.
Bethune and Joglekar (2017) Personalized T cell-mediated cancer immunotherapy: progress and challenges. Curr Opin Biotechnol 48: 142-152.
Bol et al., (2016) Dendritic Cell-Based Immunotherapy: State of the Art and Beyond. Clin Cancer Res 22(8): 1897-1906.
Borsig et al., (2002) Synergistic effects of L- and P-selectin in facilitating tumor metastasis can involve non-mucin ligands and implicate leukocytes as enhancers of metastasis. Proc Natl Acad Sci U S A 99(4): 2193-2198.
Brooks et al., (2008) Altered glycosylation of proteins in cancer: what is the potential for new anti-tumour strategies. Anticancer Agents Med Chem 8(1): 2-21.
Bukara et al., (2016) Comparative studies on osmosis based encapsulation of sodium diclofenac in porcine and outdated human erythrocyte ghosts. J Biotechnol 240: 14-22.
Butterfield (2015) Cancer vaccines. BMJ 350: h988; 28 pages.
Chen and Mellman (2013) Oncology meets immunology: the cancer-immunity cycle. Immunity 39(1): 1-10.
Chou et al., (1998) A mutation in human CMP-sialic acid hydroxylase occurred after the Homo-Pan divergence. Proc Natl Acad Sci U S A 95(20): 11751-11756.
Constantino et al., (2017) Dendritic cell-based immunotherapy: a basic review and recent advances. Immunol Res 65(4): 798-810.
Diaz et al., (2009) Sensitive and specific detection of the non-human sialic Acid N-glycolylneuraminic acid in human tissues and biotherapeutic products. PLoS One 4(1): e4241. 10 pages.
Dong et al., (2017) Formulation and Drug Loading Features of Nano-Erythrocytes. Nanoscale Res Lett 12(1): 202; 13 pages.
Dube and Bertozzi (2005) Glycans in cancer and inflammation—potential for therapeutics and diagnostics. Nat Rev Drug Discov 4(6): 477-488.
Fang et al., (2017) Cell membrane-derived nanomaterials for biomedical applications. Biomaterials. Author manuscript; available in PMC Jun. 1, 2018. Published in final edited form as: Biomaterials. Jun. 2017; 128: 69-83. 38 pages.
Farkona et al., (2016) Cancer immunotherapy: the beginning of the end of cancer? BMC Med 14: 73. 18 pages.
Fesnak et al., (2016) Engineered T cells: the promise and challenges of cancer immunotherapy. Nat Rev Cancer. Author manuscript; available in PMC Aug. 23, 2017. Published in final edited form as: Nat Rev Cancer. Aug. 23, 2016; 16(9): 566-581. 36 pages.
Finn (2017) Human Tumor Antigens Yesterday, Today, and Tomorrow. Cancer Immunol Res 5(5): 347-354.
Fuster and Esko (2005) The sweet and sour of cancer: glycans as novel therapeutic targets. Nat Rev Cancer 5(7): 526-542.
Galili (2013) Discovery of the natural anti-Gal antibody and its past and future relevance to medicine. Xenotransplantation 20(3): 138-147.
Ganguly et al., (2007) The glycocalyx protects erythrocyte-bound tissue-type plasminogen activator from enzymatic inhibition. J Pharmacol Exp Ther 321(1): 158-164.
Handy and Antonarakis (2018) Sipuleucel-T for the treatment of prostate cancer: novel insights and future directions. Future Oncol 14(10): 907-917.
Hartmaier et al., (2017) Genomic analysis of 63,220 tumors reveals insights into tumor uniqueness and targeted cancer immunotherapy strategies. Genome Med 9(1): 16; 9 pages.
Hedlund et al., (2008) Evidence for a human-specific mechanism for diet and antibody-mediated inflammation in carcinoma progression. Proc Natl Acad Sci U S A 105(48): 18936-18941.
Hu et al., (2018) Towards personalized, tumour-specific, therapeutic vaccines for cancer. Nat Rev Immunol 18(3): 168-182.
Huang and Wu (2010) Carbohydrate-based vaccines: challenges and opportunities. Expert Rev Vaccines 9(11): 1257-1274.
Jaffee et al., (2017) Future cancer research priorities in the USA: a Lancet Oncology Commission. Lancet Oncol. Author manuscript; available in PMC Oct. 10, 2018. Published in final edited form as: Lancet Oncol. Nov. 2017; 18(11): e653-e706. 120 pages.
Kim and Varki (1997) Perspectives on the significance of altered glycosylation of glycoproteins in cancer. Glycoconj J 14(5): 569-576.
Kissick (2018) Is It Possible to Develop Cancer Vaccines to Neoantigens, What Are the Major Challenges, and How Can These Be Overcome? Neoantigens as Vaccine Targets for Cancer. Cold Spring Harb Perspect Biol 10(11): a033704; 11 pages.
Kobata and Amano (2005) Altered glycosylation of proteins produced by malignant cells, and application for the diagnosis and immunotherapy of tumours. Immunol Cell Biol 83(4): 429-439.
Lesterhuis et al., (2011) Cancer immunotherapy—revisited. Nat Rev Drug Discov 10(8): 591-600.
Leviatan Ben-Arye et al., (2017) Profiling Anti-Neu5Gc IgG in Human Sera with a Sialoglycan Microarray Assay. J Vis Exp (125): 56094; 10 pages.
Li et al., (2017) Preclinical and clinical development of neoantigen vaccines. Ann Oncol 28(suppl_12): xii11-xii17.
Lindberg (1999) Glycoprotein conjugate vaccines. Vaccine 17 Suppl 2: S28-S36.
Linette and Carreno (2017) Neoantigen Vaccines Pass the Immunogenicity Test. Trends Mol Med. Author manuscript; available in PMC Oct. 1, 2018. Published in final edited form as: Trends Mol Med. Oct. 2017; 23(10): 869-871. 5 pages.
Lockhart (2003) Conjugate vaccines. Expert Rev Vaccines 2(5): 633-648.
Lollini et al., (2006) Vaccines for tumour prevention. Nat Rev Cancer 6(3): 204-216.
Luk et al., (2016) Safe and Immunocompatible Nanocarriers Cloaked in RBC Membranes for Drug Delivery to Treat Solid Tumors. Theranostics 6(7): 1004-1011.
McNeel (2018) Therapeutic Cancer Vaccines: How Much Closer Are We? BioDrugs 32(1): 1-7.
Meldolesi (2016) Ectosomes and Exosomes—Two Extracellular Vesicles That Differ Only in Some Details. Biochem Mol Biol J 2: 1; 4 pages.
Naso et al., (2017) Alpha-Gal Inactivated Heart Valve Bioprostheses Exhibit an Anti-Calcification Propensity Similar to Knockout Tissues. Tissue Eng Part A 23(19-20): 1181-1195.
Nguyen et al., (2005) Effects of natural human antibodies against a nonhuman sialic acid that metabolically incorporates into activated and malignant immune cells. J Immunol 175(1): 228-236.

* cited by examiner

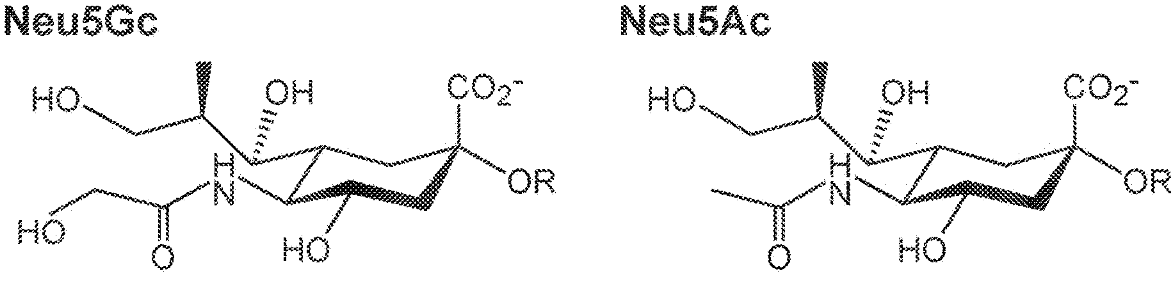
Figure 1A
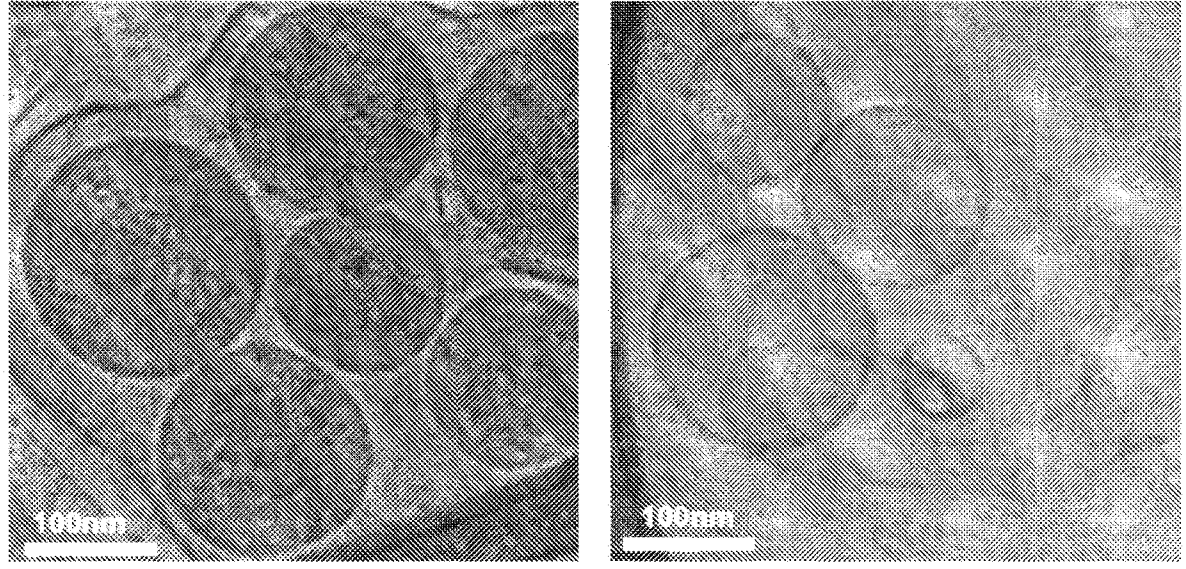
Figure 1B
Figure 1C

IMMUNOGENIC COMPOSITIONS CONTAINING N-GLYCOLYLNEURAMINIC ACID BEARING NANOPARTICLES

FIELD OF THE INVENTION

The present invention relates to an active cancer vaccine and specifically to an immunogenic composition comprising membrane vesicles that act as biomimetic nanoparticles bearing N-glycolylneuraminic acid (Neu5Gc) glycoconjugates, methods for preparing the same and uses thereof for treatment of Neu5Gc-positive tumors.

BACKGROUND OF THE INVENTION

Immunotherapy for cancer treatment has made a phenomenal leap forward in recent years, conjoining chemotherapy, hormonal therapy and targeted therapy. It generally aims to induce or expand the host anti-cancer immune response relying on the specificity of antibodies and T cells, and their ability to distinguish subtle differences between cancer and normal cells. Current cancer immunotherapy is largely implemented through targeted cellular therapeutics, immune checkpoint blockade and therapeutic cancer vaccines. Adoptive T cell therapy involves genetic manipulation of autologous T cells to express chimeric antigen receptors or engineered T cell receptors with improved specificity and efficacy. The checkpoint blockade immunotherapy impedes cancer-activated immune-inhibitory pathways by using blocking monoclonal antibodies, mainly targeting cytotoxic T lymphocyte-associated protein 4 (CTLA-4), programmed cell death protein 1 (PD1) or its ligand PD-L1. Therapeutic cancer vaccines aim at stimulating endogenous anti-tumor immune responses by harnessing recognition of tumor-associated antigens. This is mediated by professional antigen presenting cells that in turn elicit adaptive immune responses of tumor-specific cytotoxic T cells and antibodies. Current strategies are based on vaccination with tumor cells, autologous dendritic cells, proteins or peptides. So far, vaccine-based approaches had only limited success owing to challenges in designing regime and mode of delivery, selection of adjuvants, and overcoming the inhibitory tumor microenvironment, but mainly hampered due to difficulties in identifying effective target antigens. These difficulties prompted the continued search for shared antigens that would have the potential to be used in vaccines for treatment of cancer and prevention of cancer metastasis.

Although carbohydrates have long been considered to be poorly immunogenic, their enormous potential as therapeutic targets led to design of carbohydrate-based vaccines. Carbohydrate chains (glycans) are ubiquitously expressed on the surface of cells, where they are optimally located for recognition by the immune system, either for protection or for elimination. Thus, various carbohydrate-based vaccines have been actively pursued to target various bacteria, viruses, parasites or cancer cells. Cancer cells express aberrant glycosylation patterns compared to normal cells and display abnormal levels and types of carbohydrate structures on their surfaces. These carbohydrate structures, known as tumor-associated carbohydrate antigens (TACAs), can be targeted for tumor cell killing by antibodies and cytotoxic immune cells. Therapeutic cancer vaccines targeting carbohydrates could potentially assist the host immune response in the fight against cancer cells expressing TACAs.

Sialic acids (Sia) cover cell surface glycans and are over-expressed on cancer cells (Fuster, M. et al., Nature Reviews Cancer, 2005, 5(7), 526). Their altered expression on cancer cells frequently correlates with cancer progression and/or metastasis (Padler-Karavani, V. Cancer Letters, 2014, 352(1), 102-112). N-acetylneuraminic acid (Neu5Ac) and its hydroxylated form, N-glycolylneuraminic acid (Neu5Gc) are the two major Sia forms in mammals. While humans cannot synthesize Neu5Gc due to a specific inactivation of the cytidine monophosphate-N-acetylneuraminic acid hydroxylase (CMAH) gene, this non-human Sia incorporates into human cells through consumption of red meat and dairy, thereby accumulating mostly on human carcinomas (Amon, R. et al., Carbohydrate Research, 2014, 389, 115-122). Thus, Neu5Gc expression on tumor cells generates a variety of neoantigens that could potentially be targeted for immunotherapy. Passive transfer of anti-Neu5Gc antibodies for cancer immunotherapy has been previously reported (Padler-Karavani, V. et al., Cancer Research, 2011, 71(9), 3352-3363). However, circulating anti-Neu5Gc antibodies have been reported to have dualistic and opposing responses with both tumor growth stimulatory characteristics and tumor growth inhibitory characteristics.

U.S. Pat. No. 6,149,921 provides uses for N-glycolylated gangliosides and N-acetylated gangliosides, or derivatives and/or oligosaccharides thereof. U.S. Pat. No. 6,149,921 further provides methods of obtaining such gangliosides, as well as vaccine compositions comprising said gangliosides. The gangliosides may be coupled to carriers and may be accompanied by adjuvants. The vaccine compositions can be used in the treatment of breast cancers, whereby the gangliosides are used to elicit an immune response to corresponding gangliosides on breast tumor cells.

U.S. Pat. No. 8,591,917 discloses vaccine compositions in which gangliosides and the outer membrane protein complex (OMP) of *Neisseria meningitidis* were combined to form very small size proteoliposomes (VSSP) to be administered subcutaneously. These compositions do not require the use of any additional adjuvant. The described compositions allow the immunological treatments with gangliosides, particularly N-AcGM3/VSSP and N-GcGM3/VSSP showing advantages due to the less aggressive reaction in the site of injection and can be used in a simpler way and better for the patients.

U.S. Pat. No. 9,423,401 discloses sialylated glycans and antibodies that specifically bind to them. The compositions and methods for using them are useful for early detection and diagnosis of cancer.

However, there remains an unmet need for an efficient active cancer vaccine composition targeting the Neu5Gc-neoantigens for a potent and sustained anti-Neu5Gc immune response.

SUMMARY OF THE INVENTION

The present invention provides compositions comprising glycolylneuraminic acid (Neu5Gc) exposed on the surfaces of specific acellular membrane particles. The compositions can induce beneficial immunological responses in subjects bearing tumors that express Neu5Gc.

The present invention is based in part on the finding that immunotherapy that targets tumor-associated carbohydrate antigens (TACAs), in particular Neu5Gc, can potentially assist the host immune response in the fight against cancer cells expressing TACAs. In contrast with passive transfer of anti-Neu5Gc antibodies that has dualistic and opposing responses, it was surprisingly found that active immunization utilizing the immunogenic compositions as described in the present invention induced a potent and sustained anti- Neu5Gc immune response, and lead to a significant inhibition of Neu5Gc-positive tumor growth in vivo.

Advantageously the membrane vesicles of the present invention are derived from natural membranes of cells expressing Neu5Gc and therefore comprise a plurality of Neu5Gc glycoconjugate structures, i.e., the Neu5Gc molecules are coupled to different glycoconjugates, leading to highly diverse, robust and persistent anti-Neu5Gc IgG response. In addition, the preparation methods of these biomimetic nanoparticles eliminate the need of pre-isolation of Neu5Gc glycoconjugates and subsequent anchoring on the surface of the carrier particles.

According to one aspect, the present invention provides an immunogenic composition comprising a delivery particle derived from the membrane of a eukaryotic cell expressing N-glycolylneuraminic acid (Neu5Gc) glycoconjugates, wherein the Neu5Gc is exposed on the outer surface of the delivery particle, wherein the delivery particle has an average hydrodynamic diameter in the submicron range.

According to one aspect, the present invention provides an immunogenic composition comprising a plurality of membrane vesicles bearing Neu5Gc glycoconjugates, wherein the Neu5Gc glycoconjugates are exposed on the outer surface of the membrane vesicles. These membrane vesicles are derived from the membranes of eukaryotic cells expressing Neu5Gc, wherein the membrane vesicles have an average hydrodynamic diameter in the submicron range. In particular these membrane vesicles are derived from the outer plasma membranes of eukaryotic cells expressing Neu5Gc, wherein the membrane vesicles have an average hydrodynamic diameter in the submicron range.

According to another aspect, the present invention provides a vaccine comprising an immunogenic composition comprising a plurality of membrane vesicles bearing Neu5Gc glycoconjugates, wherein the Neu5Gc glycoconjugates are exposed on the outer surface of the membrane vesicles, wherein the membrane vesicles are derived from the outer plasma membranes of eukaryotic cells expressing Neu5Gc, wherein said membrane vesicles have an average hydrodynamic diameter in the submicron range.

In some embodiments, the vaccine is for use in treating cancer. In specific embodiments, the cancer is Neu5Gc-positive.

In some embodiments, the membrane vesicle is selected from the group consisting of a cell ghost, an exosome and an ectosome. Each possibility represents a separate embodiment of the present invention. In some embodiments, the membrane vesicle is a cell ghost.

According to another aspect, the present invention provides a method for preparing cell ghosts displaying Neu5Gc glycoconjugates on the outer surface, the method comprising the steps of:

a) providing a first composition comprising a plurality of isolated eukaryotic cells expressing Neu5Gc glycoconjugates on their outer plasma membrane surface;
b) removing the intracellular contents by membrane rupture in a hypotonic buffer and centrifugation to remove soluble proteins, thereby obtaining a second composition; and
c) washing the second composition and resuspending in double distilled water (DDW) to obtain the cell ghosts.

In certain embodiments, the membrane vesicle has an average hydrodynamic diameter within the range of 30-1000 nm, 80-950 nm, 150-900 nm, or 200-800 nm. Each possibility represents a separate embodiment of the present invention. In certain embodiments, the cell ghost has an average hydrodynamic diameter within the range of 30-1000 nm, 80-950 nm, 150-900 nm, or 200-800 nm. Each possibility represents a separate embodiment of the present invention.

In various embodiments, the eukaryotic cell from which the membrane vesicle is derived, is a mammalian cell. In further embodiments, the mammalian cell is a non-human cell. In some embodiments, the mammalian cell is a non-genetically modified cell that naturally expresses Neu5Gc-glycoconjugates. In specific embodiments, the immunogenic composition comprises a plurality of membrane vesicles bearing Neu5Gc glycoconjugates, the membrane vesicles are derived from the membrane of a non-human mammalian cell, wherein the non-human mammalian cell is a non-genetically modified cell that naturally expresses Neu5Gc-glycoconjugates.

In further embodiments, the mammalian cell is selected from the group consisting of red blood cells (RBCs), mesenchymal stem cells (MSCs), platelets and cancer cells. In some embodiments, the mammalian cell is selected from the group consisting of RBCs, platelets and cancer cells. In other embodiments, the mammalian cell is selected from the group consisting of RBCs, platelets and MSCs. Each possibility represents a separate embodiment of the present invention.

In some embodiments, the mammalian cell is a non-genetically modified mammalian cell selected from the group consisting of RBCs, MSCs, platelets, cancer cells or any cell type expressing the Neu5Gc antigen. Each possibility represents a separate embodiment of the present invention.

In specific embodiments, the non-genetically modified mammalian cell is a red blood cell (erythrocyte). In further specific embodiments, the non-genetically modified mammalian cell is a non-human red blood cell. In yet further specific embodiments, the non-human red blood cell is porcine-derived.

In certain embodiments, the RBC is derived from porcine strain that is deficient in the GGTA1 gene ($Ggta1^{-/-}$ knockout) encoding the α1,3-galactosyltransferase (α1,3GT).

In some embodiments, the membrane vesicle is a delivery particle. In specific embodiments, said delivery particle further comprises an inner core, wherein the inner core is coated by the natural membrane derived from the eukaryotic cell. In specific embodiments, the inner core comprises a particle selected from the group consisting but not limited to polymeric particles, magnetic particles and metallic particles. Each possibility represents a separate embodiment of the present invention. In further specific embodiments, the inner core comprises a nanoparticle selected from the group consisting but not limited to polymeric nanoparticles, magnetic nanoparticles and metallic nano particles. Each possibility represents a separate embodiment of the present invention.

In certain embodiments, the immunogenic composition further comprises at least one additional tumor-associated antigen, wherein the at least one additional tumor-associated antigen is exposed on the outer surface of the membrane vesicle. In further embodiments, the additional tumor-associated antigen is carbohydrate-based.

In certain embodiment, the immunogenic composition further comprises a targeting agent conjugated to said membrane vesicle to direct the antigen to a particular in vivo location or particular cell population.

In some embodiments, the immunogenic composition further comprises an adjuvant approved for human use.

According to some aspects and embodiments, the present invention provides a method of stimulating an anti-cancer immune response in a subject, the method comprising administering the immunogenic composition as described above in various embodiments thereof, to the subject. According to some aspects and embodiments, the present invention provides a method of stimulating an anti-cancer immune response in a subject, the method comprising administering the vaccine composition in various embodiments thereof, to the subject. In various embodiments, said vaccine is administered by a route selected from the group consisting but not limited to oral administration, subcutaneous administration, aerosol administration, intraperitoneal injection, intravenous injection and intramuscular injection. Each possibility represents a separate embodiment of the present invention. In further embodiments, said method of stimulating an anti-cancer immune response in a subject comprises repeated administrations.

In some embodiments, the method of stimulating an anti-cancer immune response in a subject further comprises administering an additional immunotherapeutic drug. In some embodiments, the method of stimulating an anti-cancer immune response in a subject further comprises administering at least one additional immunotherapeutic drug. In some embodiments, the vaccine composition and the additional immunotherapeutic drug are administered substantially simultaneously, concurrently, alternately, successively or according to overlapping schedules.

In some embodiments, the immunotherapeutic drug is an immune checkpoint inhibitor. In certain embodiments the immune checkpoint inhibitor is selected from programmed cell death protein 1 (PD-1) inhibitor, programmed death-ligand 1 (PD-L1) inhibitor and cytotoxic T lymphocyte antigen-4 (CTLA-4) inhibitor. Each possibility represents a separate embodiment of the present invention.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIGS. 1A-1G present physiochemical characterization of porcine-derived nano-ghosts (NG) that express either Neu5Gc glycoconjugates ($NG^{pos}$), or control non-immunogenic Neu5Ac glycoconjugates ($NG^{neg}$). FIG. 1A is a schematic representation of the chemical structures of Neu5Gc and Neu5Ac. FIGS. 1B-1C show transmission electron microscopy (TEM) images of $NG^{pos}$ (FIG. 1B) and $NG^{neg}$ (FIG. 1C). FIG. 1D is a bar graph presenting the zeta potential of $NG^{pos}$ and $NG^{neg}$. FIG. 1E is a bar graph presenting the mean sizes of $NG^{pos}$ and $NG^{neg}$ as measured by DLS. FIGS. 1F-1G are histograms demonstrating the size distribution of $NG^{pos}$ (FIG. 1F) and $NG^{neg}$ (FIG. 1G) as measured by DLS.

FIG. 2A shows silver staining of freshly prepared NG. FIG. 2B shows Western blot analysis of sialic acid (Sia) content of $NG^{pos}$ and $NG^{neg}$ with or without pre-treatment of the blot with mild periodate oxidation. Sia-binding proteins: SNA, MAL-II and anti-Neu5Gc IgY. FIGS. 2C-2D demonstrate the Sia surface expression on $NG^{pos}$ and $NG^{neg}$ after a freeze-thaw cycle, analyzed by microarray (FIG. 2C) and by ELISA (FIG. 2D).

FIG. 3A is a schematic representation of the immunization regime. Thick black arrow indicates immunization with $NG^{pos}$ or $NG^{neg}$ emulsified in FCA; thin black arrows indicate injections of $NG^{pos}$ or $NG^{neg}$ emulsified in FIA; Grey arrows indicate mouse sera collection. FIGS. 3B-3C are line graphs presenting the analysis of sera samples by sialoglycan microarrays containing diverse sialoglycans: FIG. 3B shows the average IgG response for mono-sialylated Neu5Gc-glycans and Neu5Ac-glycans. FIG. 3C shows the response to individual Neu5Gc-glycans.

FIG. 4A is a schematic representation of an additional immunization regime based on the initial B2W regime. Thick black arrow indicates immunization with $NG^{pos}$ or $NG^{neg}$ in FCA; thin black arrows indicate injections of $NG^{pos}$ or $NG^{neg}$ in FIA; Grey arrows indicate mouse sera collection. FIGS. 4B-4C are line graphs showing the analysis of sera samples after immunization with $NG^{pos}$ according to the regime presented in FIG. 4A, obtained by sialoglycan microarrays containing diverse sialoglycans: FIG. 4B shows the average IgG response for mono-sialylated Neu5Gc-glycans and Neu5Ac-glycans, and FIG. 4C shows the response to individual Neu5Gc-glycans. FIG. 4D is a line graph showing the average IgG response for mono-sialylated Neu5Gc-glycans and Neu5Ac-glycans after immunization with $NG^{neg}$ according to the regime presented in FIG. 4A. FIG. 4E is a schematic representation of B1W immunization regime. Thick black arrow indicates immunization with $NG^{pos}$ in FCA; thin black arrows indicate injections of $NG^{pos}$ in FIA; Grey arrows indicate mouse sera collection. FIGS. 4F-4G are line graphs showing sialoglycan microarrays analysis of sera samples after immunization with $NG^{pos}$ according to the regime presented in FIG. 4E: FIG. 4F shows the average IgG response for mono-sialylated Neu5Gc-glycans and Neu5Ac-glycans, and FIG. 4G shows the response to individual Neu5Gc-glycans.

FIG. 6A is a schematic representation of the experimental design based on the B2W regime. Upper grey arrow indicates subcutaneous inoculation of Neu5Gc-positive tumor at week 5.5. FIG. 6B is a line graph presenting the tumor volume measurements.

FIG. 7A is a schematic representation of the experimental design based on the B1W regime. Upper grey arrow indicates subcutaneous inoculation of Neu5Gc-positive tumor at week 7.5. FIG. 7B is a line graph presenting the tumor volume measurements. FIG. 7C is a line graph showing the average response against all Neu5Gc glycans in mice immunized with $NG^{pos}$ or $NG^{neg}$, with or without inoculation of tumor (w Tumor or w/o Tumor). FIGS. 7D-7F are line graph showing the response to individual Neu5Gc-glycans, in mice immunized with $NG^{pos}$ and exposed to Neu5Gc-positive tumor (FIG. 7D); in mice immunized with $NG^{pos}$ without exposure to Neu5Gc-positive tumor (FIG. 7E); and in mice immunized with $NG^{neg}$ and exposed to Neu5Gc-positive tumor (FIG. 7F).

FIGS. 10A, 10C and 10E show the average IgG response against all Neu5Gc-glycans and all Neu5Ac-glycans in group 1 (FIG. 10A), group 2 (FIG. 10C) and group 3 (FIG. 10E). FIGS. 10B, 10D and 10F show the average IgG response against individual Neu5Gc-glycans in group 1 (FIG. 10B), group 2 (FIG. 10D) and group 3 (FIG. 10F).

DETAILED DESCRIPTION OF THE INVENTION

Figures 1D, 1E, 1F:
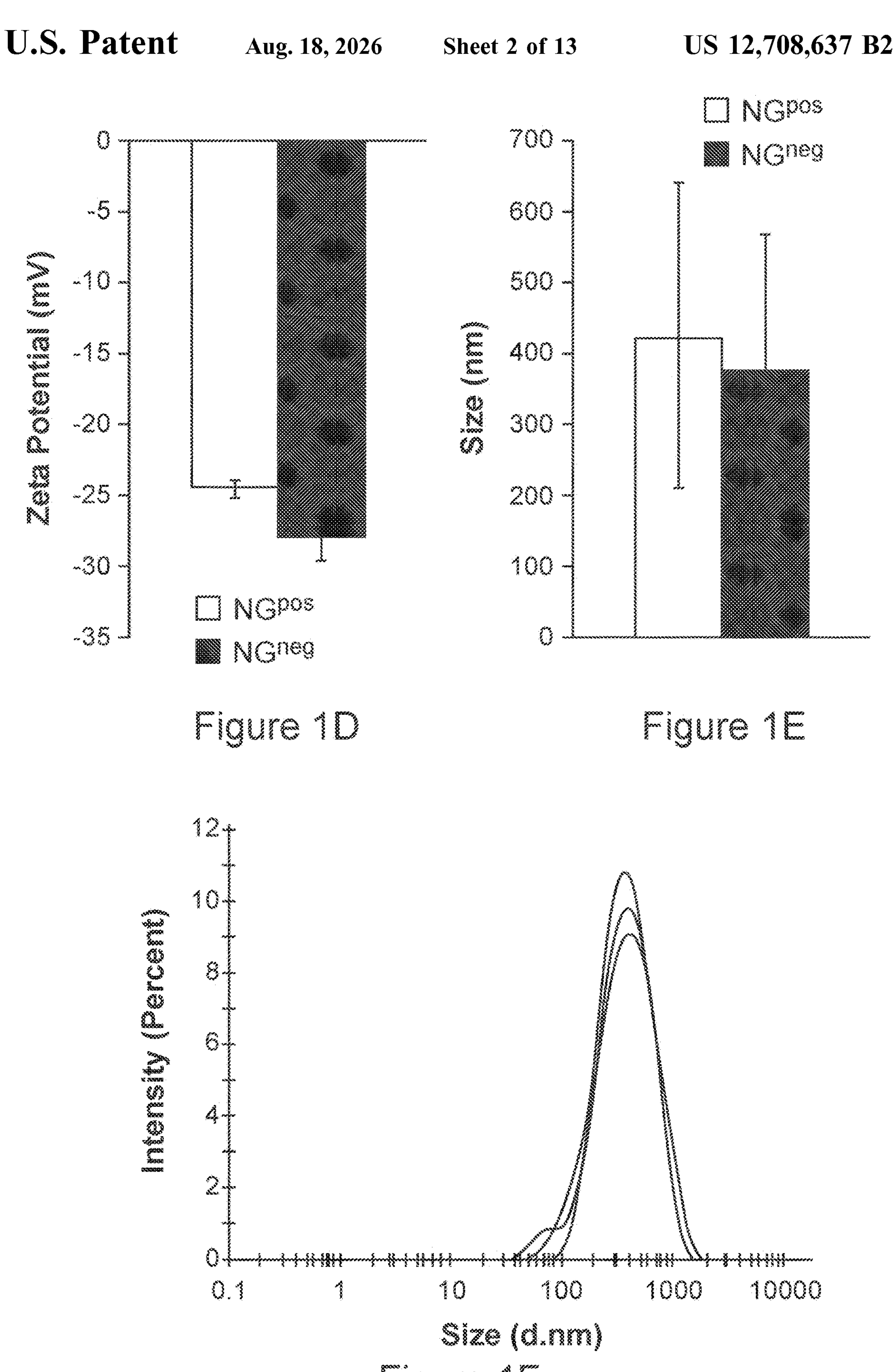

The present invention provides therapeutic vaccine compositions for sustained and robust anti-cancer immune response in a patient or subject, based on biomimetic nanoparticles comprising N-glycolylneuraminic acid (Neu5Gc)-glycoconjugates, wherein Neu5Gc is exposed on the outer surface of the biomimetic nanoparticles, thereby stimulating an endogenous anti-tumor immune response by harnessing Neu5Gc recognition.

The present invention is based in part on the finding that immunotherapy that targets tumor-associated carbohydrate antigens (TACAs), in particular Neu5Gc, can potentially assist the host immune response in the fight against cancer cells expressing TACAs. However, passive transfer of anti-Neu5Gc antibodies has dualistic and opposing responses: while high dose anti-Neu5Gc antibodies inhibits tumor growth, a low dose treatment actually promotes tumor growth. Furthermore, the shift between these opposing dosage effects occur at a very narrow range of even only two-fold changes. In contrast, the active immunization utilizing the immunogenic composition as described in the present invention induces a potent and sustained anti-Neu5Gc immune response, thereby leading to a significant tumor growth inhibition.

The term "active immunization" as used herein means that an immunogen is administered to an individual, eliciting the individual's humoral and/or cell-mediated adaptive immune responses. In contrast, "passive immunotherapy" utilizes only the antibody arm of the immune system. According to one aspect, the present invention provides an immunogenic composition comprising a plurality of membrane vesicles displaying Neu5Gc glycoconjugates, wherein the membrane vesicles are derived from the membrane of a eukaryotic cell expressing Neu5Gc glycoconjugates, wherein the Neu5Gc is exposed on the outer surface of the membrane vesicles, wherein the membrane vesicles have an average hydrodynamic diameter in the submicron range.

As used herein, the term "immunogenic composition" means a composition that is capable of being recognized by the immune system, resulting in the generation of a specific immune response (i.e., has immunogenic activity) when administered alone or with a pharmaceutically acceptable agent, to a subject.

According to one aspect, the present invention provides a vaccine comprising an immunogenic composition comprising a plurality of membrane vesicles bearing Neu5Gc glycoconjugates, wherein the Neu5Gc glycoconjugates are exposed on the outer surface of the membrane vesicles, wherein the membrane vesicles are derived from the plasma membranes of eukaryotic cells expressing Neu5Gc, wherein said membrane vesicles have an average hydrodynamic diameter in the submicron range.

In some embodiments, the vaccine is for use in treating cancer. In specific embodiments, the cancer is Neu5Gc-positive.

Without being bound to any theory or mechanism, it is hypothesized that after administration, the immunogenic composition of the present invention promotes, inter alia, the generation of anti-Neu5Gc antibodies which mediate inhibition of tumor growth, for example by migration to the tumor site.

As used herein, the term "membrane vesicle(s)" denotes any vesicle composed of a lipid bilayer derived from the membrane of a eukaryotic cell, thereby possessing inherent membrane-associated characteristics. In some embodiments, the membrane vesicle is a particle selected from the group consisting of: cell ghosts, liposomes, exosomes and ectosomes. In some embodiments, the membrane vesicle is a particle selected from the group consisting of: cell ghosts, exosomes and ectosomes. In some embodiments, the membrane vesicle is a particle selected from the group consisting of cell ghosts and ectosomes. In some embodiments, the membrane vesicle is a cell ghost. In some embodiments, the membrane vesicle is an exosome. In some embodiments, the membrane vesicle is an ectosome.

The term "cell ghost" as used herein refers to a substantially empty membrane vesicle produced from plasma membrane of a cell. The cell ghost retains plasma cell membrane and lipid raft integrity of the original cell but renders the cell empty and non-viable. The terms "empty" and "substantially empty" as interchangeably used herein mean that the cell ghost contains little or no intracellular components. In a non-limiting example, the cell ghost lack defined nuclear and cytoplasmic details. In another non-limiting example, the cell ghost lack intracellular proteins.

As used herein, the term "exosome" refers to an extracellular vesicle that is released from a cell upon fusion of a multivesicular body (MVB) with the plasma membrane. Usually, exosomes are smaller than most other extracellular vesicles, having a diameter of between about 30 nm to several hundred nanometers. Exosomes can be purified from cell culture supernatants by differential centrifugation, ultrafiltration, or adsorption on a support or by any other method known in the art.

The term "ectosome" as used herein refers to a type of extracellular vesicle that is released from cells by direct budding from the cell surface. Ectosomes are usually larger than exosomes, having a dimeter varying between about 100 nm to about 1000 nm.

The term "liposome" as used herein encompasses any compartment surrounded by a lipid bilayer. In some embodiments, the term liposome is a unilamellar vesicle composed of a single lipid bilayer and typically includes unilamellar vesicles having a diameter in the range of about 20 to about 400 nm. In alternative embodiments, liposomes can include multilamellar vesicles (MLV), large unilamellar vesicles (LUV), and small unilamellar vesicles (SUV). In some embodiments, the liposomes are cell-derived liposomes.

The terms "bearing Neu5Gc" and "displaying Neu5Gc" are used interchangeably herein and refer to biomimetic membrane vesicles/particles in which the Neu5Gc antigen is exposed on the outer surface. Once administered to the body, such particles present the Neu5Gc antigen to cells of the immune system.

The term "glycoconjugate(s)" as used herein means compound(s) containing a carbohydrate moiety. Examples for glycoconjugates are glycoproteins, glycopeptides, proteoglycans, peptidoglycans, glycolipids, GPI-anchors, lipopolysaccharides. Accordingly, the term "Neu5Gc glycoconjugates" means glycoconjugates that are covalently bound to the Neu5Gc antigen.

In some embodiments, diverse Neu5Gc glycoconjugates are exposed on the surface of the membrane vesicles. In some embodiments, a plurality of different Neu5Gc glycoconjugates are exposed on the surface of the membrane vesicles, wherein said different Neu5Gc glycoconjugates differ in the specific glycoconjugate attached to the Neu5Gc antigen.

As used herein, the term "submicron" refers to dimensions of from 10 nm up to 1 μm. In some embodiments, the term "submicron" refers to dimensions of above 10 nm and below 1 μm.

The Neu5Gc glycoconjugates may be either covalently attached to, or non-covalently integrated in the lipid bilayer of the particle derived from the membrane of a eukaryotic cell. Each possibility represents a separate embodiment of the present invention. In some embodiments, the Neu5Gc glycoconjugates are covalently attached to the lipid bilayer of the membrane vesicle. In other embodiments, the Neu5Gc glycoconjugates are non-covalently integrated within the lipid bilayer of the membrane vesicle, wherein the Neu5Gc antigen is exposed on the outer surface of said lipid bilayer.

According to some aspects, the present invention provides a method for preparing cell ghosts expressing Neu5Gc glycoconjugates on the outer surface, the method comprising the steps of:

a) providing a first composition comprising a plurality of isolated eukaryotic cells expressing Neu5Gc glycoconjugates on their outer membrane surface;
b) removing the intracellular contents by membrane rupture in a hypotonic buffer and centrifugation to remove soluble proteins, thereby obtaining a second composition; and
c) washing the second composition and resuspending in double distilled water (DDW) to obtain the cell ghosts.

In certain embodiments, the membrane vesicles of the present invention are in the average hydrodynamic diameter range of 30-1000 nm, 50-1000 nm, 80-1000 nm, 120-1000 nm, 150-1000 nm, 200-800 nm, or 200-650 nm. Each possibility represents a separate embodiment of the present invention. In some embodiments, the membrane vesicles have an average hydrodynamic diameter within the range of 30-1000 nm. In some embodiments, the membrane vesicles have an average hydrodynamic diameter within the range of 80-950 nm. In some embodiments, the membrane vesicles have an average hydrodynamic diameter within the range of 100-900 nm. In some embodiments, the membrane vesicles have an average hydrodynamic diameter within the range of 150-900 nm. In some embodiments, the membrane vesicles have an average hydrodynamic diameter within the range of 200-800 nm. In some embodiments, the membrane vesicles have an average hydrodynamic diameter within the range of 250-700 nm. In some embodiments, the membrane vesicles have an average hydrodynamic diameter within the range of 300-650 nm. In some embodiments, the membrane vesicles have an average hydrodynamic diameter within the range of 350-600 nm.

In some embodiments, the cell ghosts have an average hydrodynamic diameter in the submicron range. In some embodiments, the cell ghosts have an average hydrodynamic diameter within the range of 30-1000 nm, 80-950 nm, 100-900 nm, 150-900 nm, 200-800 nm, 250-700 nm, 300-650 nm or 350-600 nm. In some embodiments, the cell ghosts have an average hydrodynamic diameter within the range of 30-1000 nm, 80-950 nm, 150-900 nm or 200-800 nm. Each possibility represents a separate embodiment of the present invention.

The effective average particle size depends on factors such as the intended route of administration, formulation, solubility, toxicity and bioavailability of the compound. Any method known in the art can be used to determine the size of the membrane vesicle. For example, dynamic light scattering (DLS) for determining the hydrodynamic diameter of the particles and cryo-transmission electron microscopy (cryo-TEM) for determining the accurate geometric nanoparticle size.

The term "hydrodynamic diameter", as used herein, generally refers to the effective diameter of a hydrated particle in solution, corresponding to the diameter of a sphere with equal mobility in solution. Accordingly, the hydrodynamic diameter of a particle includes contributions from the solvation sphere. In some embodiments, a hydrodynamic diameter is used to describe the measured size of the membrane vesicles in solution. In certain embodiments, hydrodynamic diameter may be determined by DLS size measurement.

In some embodiments, the membrane vesicles are detectible by transmission electron microscope. In some embodiments, the accurate geometric size of the membrane vesicle is within a range selected from the group consisting of 20-900 nm, 30-850 nm, 50-800 nm, 60-750 nm, 70-700 nm, 80-600 nm 90-500 nm, and 100-400 nm. Each possibility represents a separate embodiment of the present invention.

In some embodiments of the present invention, the eukaryotic cell is mammalian In some embodiments, the mammalian cell is a human cell. In other embodiments, the mammalian cell is non-human. Non-human mammalian cells can be derived from varied species of mammals, including but not limited to bovine, equine, porcine, canine, deer, sheep, mouse, rat, rabbit, ferret, buffalo and any species listed by Wilson, D. E. and Reeder, D. M., Mammal Species of the World, Smithsonian Institution Press, (1993), hereby incorporated by reference herein.

In one embodiment, the eukaryotic cell is genetically engineered to express Neu5Gc on its surface. In another embodiment, the eukaryotic cell is a non-genetically engineered cell that naturally expresses Neu5Gc on its surface.

In some embodiments, the membrane vesicles are derived from the outer plasma membrane of a eukaryotic cell, wherein the eukaryotic cell is a non-genetically modified mammalian cell that naturally expresses Neu5Gc-glycoconjugates on its surface. In further embodiments, the eukaryotic cell is a non-human mammalian cell wherein the non-human mammalian cell is a non-genetically modified cell that naturally expresses Neu5Gc-glycoconjugates on its surface.

As used herein, the term "naturally expresses" refers to a cell that endogenously expresses the relevant antigen without exogenous modification.

In some embodiments, the mammalian cell is selected from the group consisting of a red blood cells (RBCs, erythrocytes), mesenchymal stem cells (MSCs), platelets and cancer cells. In some embodiments, the mammalian cell is selected from the group consisting of RBCs, MSCs and platelets. In some embodiments, the mammalian cell is selected from the group consisting of RBCs and platelets. Each possibility represents a separate embodiment of the present invention. In some embodiments, the mammalian cell is a red blood cell. In some embodiments, the non-genetically modified mammalian cell is selected from the group consisting of RBCs, MSCs, platelets, cancer cells or any cell type expressing the N-glycolylneuraminic acid antigen. In some embodiments, the non-genetically modified mammalian cell is selected from the group consisting of RBCs, MSCs and platelets. In some embodiments, the non-genetically modified mammalian cell is selected from the group consisting of RBCs and platelets. Each possibility represents a separate embodiment of the present invention.

In one specific embodiment, the mammalian cell is a cancer cell naturally expressing Neu5Gc on its surface. In another embodiment, the mammalian cell is a cancer cell presenting Neu5Gc on its surface. While humans cannot synthesize Neu5Gc due to a specific inactivation of the cytidine monophosphate-N-acetylneuraminic acid hydroxylase (CMAH) gene, the non-human Neu5Gc may be incorporated in human cells through consumption of red meat and dairy, thereby accumulating mostly on human carcinomas. In one specific embodiment, the mammalian cell is a human cancer cell expressing Neu5Gc on its surface. In another embodiment, the mammalian cell is a human cancer cell presenting Neu5Gc on its surface. In some embodiment, the cancer cell is an autologous tumor cell isolated from an individual's own tumor.

In some embodiments, the membrane vesicle is a nanoparticle. In some embodiments, the membrane vesicle is a cell ghost, wherein the cell ghost is a nano-ghost. The term "nanoparticle" as used herein refers to a nanometer-sized particle (i.e., nanometer-sized membrane vesicle) having a diameter of between about 1 nm to about 1000 nm. The term "nano-ghost" as used herein refers to a cell ghost having a diameter of between about 20 nm to about 1000 nm.

According to some embodiments, the membrane vesicle is a biomimetic cell ghost derived from the membrane of a non-human mammalian cell naturally expressing Neu5Gc on its surface, wherein said non-human mammalian cell is selected from the group consisting but not limited to red blood cells, mesenchymal stem cells, platelets and cancer cells. Each possibility represents a separate embodiment of the present invention.

In some embodiments, the membrane vesicle is a cell ghost wherein the cell ghost is substantially empty. In some embodiments, the cell ghost is devoid of intracellular constituents. In some embodiments, the cell ghost is devoid of at least one intracellular constituent selected from the group consisting of cell nucleus, intracellular proteins, cytoskeleton elements, DNA and RNA. Each possibility represents a separate embodiment of the present invention.

The preparation of biomimetic cell ghosts/nano-ghosts is mainly based on plasma membrane extraction from the cells. It typically includes steps for cell lysis and membrane purification. To minimalize probable denaturation of the membrane-oriented proteins, membrane extraction must be as gentle as possible. The detailed procedures are known in the art and should be modified depending on whether the source cells contain nucleus or not.

To extract the membrane of eukaryotic nucleus-free cells such as erythrocytes (red blood cells; RBCs) and platelets, the cells have to be initially isolated from whole blood using blood fraction isolation kits and/or centrifugation-based methodologies. Isolated cells are then lysed with either a hypotonic treatment or repeated freeze-thaw cycles and soluble proteins can be removed by centrifugation, to obtain purified biomimetic cell ghosts.

Compared with nucleus-free cells, membrane extraction and purification from cells having nucleus are more complicated and may include the steps of harvesting sufficient amount of target cells; lysis with hypotonic treatment and/or mechanical membrane destruction (e.g. extrusion); Removing intracellular biomacromolecules, intracellular vesicles and nucleus by discontinuous gradient centrifugation; sonication and extrusion through porous membrane to obtain the emptied cell ghosts.

Among the various types of cells, RBCs are attractive candidates for generating biomimetic cell ghosts/nano-ghosts. RBCs are biconcave disc shaped cells (~7.8 μm×~2.5 μm) that lack nucleus, with plasma membrane surface area of ~160 $\mu m^2$. RBCs are resistant to adhesion to endothelium, partly mediated by their glycocalyx that is abundantly covered with negatively charged sialic acids. Importantly, RBCs are labile to changes in osmotic pressure and easily hemolyzed under hypotonic buffer conditions. In addition, RBCs are highly biocompatible and display membrane proteins (e.g. CD47) that enable significantly prolonged circulation in the blood (up to 120 days).

In some embodiments, the membrane vesicle comprises the cell surface glycoprotein protein CD47, wherein the CD47 is integrated in the lipid bilayer of said membrane vesicle.

In certain embodiments, the membrane vesicles are cell ghosts/nano-ghosts generated from RBCs. In certain embodiments, the cell ghosts/nano-ghosts are generated from mammalian RBCs. In certain embodiments, the cell ghosts/nano-ghosts are generated from non-human mammalian RBCs. In specific embodiments, the non-human mammalian RBCs are porcine-derived, wherein the porcine-derived RBCs naturally express Neu5Gc-glycoconjugates.

In further embodiments, the immunogenic composition of the present invention comprises a plurality of membrane vesicles derived from the membranes of RBCs derived from porcine strain that is deficient in the GGTA1 gene ($Ggta1^{-/-}$ knock-out) encoding the α1,3-galactosyltransferase (α1,3GT), in order to eliminate the αGal that is an immunogenic xenoantigen in humans, and against which all humans have circulating anti-Gal antibodies.

In specific embodiments, the immunogenic composition of the present invention comprises a plurality of membrane vesicles derived from the membranes of RBCs of porcine $Ggta1^{-/-}$ knock-out strain, wherein the average hydrodynamic diameter of the membrane vesicles is within the range of 30-1000 nm, 50-1000 nm, 80-1000 nm, 80-950 nm, 120-1000 nm, 150-1000 nm, 150-900 nm, 200-800 nm, 200-650 nm, 300-650 nm or 350-600 nm. Each possibility represents a separate embodiment of the present invention.

In some embodiments, the membrane vesicles are stable after several freeze-thaw cycles. In some embodiments, the membrane vesicles are stable after one freeze-thaw cycle. In some embodiments, the membrane vesicles retain their immunogenic activity after one freeze-thaw cycle.

In some embodiments, the membrane vesicles are devoid of exogenous molecules introduced into the lumen and thereby encapsulated therein. More specifically, the membrane vesicles are not loaded with an exogenous molecule selected from a drug, an enzyme, a nucleic acid, an antibody or a polypeptide. In some embodiments, the membrane vesicles are devoid of an exogenous drug encapsulated therein. In some embodiments, the exogenous drug is selected from a synthetic drug and a genetically engineered drug. Each possibility represents a separate embodiment of the present invention. As used herein, the term "exogenous molecule" or "exogenous drug" refers to a molecule/drug from a source which is external to the original cell from which the membrane vesicle is derived.

According to some aspects and embodiments, the present invention provides a method for preparing nano-ghosts displaying Neu5Gc antigen on their outer surface, the method comprising the steps of:

a) purifying erythrocytes from fresh blood of a mammalian subject, wherein the erythrocytes express the Neu5Gc antigen;
b) removing the intracellular contents by membrane rupture in a hypotonic buffer or by repeated freeze-thaw cycles, and centrifugation to remove soluble proteins; and
c) washing the emptied erythrocytes and resuspending in double distilled water to obtain the glycoproteolipid nano-ghost vesicles.

According to some embodiments, the present invention provides a method for preparing nano-ghosts displaying Neu5Gc antigen on their outer surface, the method comprising the steps of:

a) purifying erythrocytes from fresh blood of a porcine $\alpha$-Gal knockout strain by centrifugation;
b) removing the intracellular contents by membrane rupture in a hypotonic buffer and centrifugation to remove soluble proteins; and
c) washing the emptied erythrocytes and resuspending in double distilled water to obtain the glycoproteolipid nano-ghost vesicles.

In this technique, the hypotonic rupture alone reduces the vesicle size while keeping the right-side-out configuration, without trapping the antigenic Neu5Gc inside the vesicles. This is advantageous compared with other methods that involve sonication or mechanic extrusion and therefore might form flipped inside-out nano-ghosts.

According to some embodiments, the membrane vesicle is a delivery particle further comprising an inner core. According to specific embodiments, the membrane vesicle further comprises an inner core, wherein the inner core is coated by the lipid bilayer of said membrane vesicle. In specific embodiments, the lipid bilayer that coats the inner core is derived from non-human cells, wherein the non-human cells naturally express Neu5Gc-glycoconjugates. In some embodiments, said inner core comprises a particle selected from the group consisting but not limited to polymeric particles, magnetic particles and metallic particles. Each possibility represents a separate embodiment of the present invention. In some embodiments, said inner core comprises a polymeric particle. In some embodiments, said inner core comprises a magnetic particle. In some embodiments, said inner core comprises a metallic particle. In some embodiments, the inner core comprises a nanoparticle selected from the group consisting but not limited to polymeric nanoparticles, magnetic nanoparticles and metallic nanoparticles. Each possibility represents a separate embodiment of the present invention.

The preparation procedures of submicron particles comprising an inner core coated by a natural membrane are known in art and in general, involve three steps: (a) membrane extraction and purification from cells; (b) preparation of core particle, and (c) fusion of the two into a single core-shell particle.

In certain embodiments, the immunogenic composition further comprises additional tumor-associated antigens, wherein the additional tumor-associated antigens are exposed on the outer surface of the membrane vesicle. In some embodiments, the immunogenic composition further comprises an additional tumor-associated antigen, wherein the additional tumor-associated antigen is exposed on the outer surface of the membrane vesicle. In some embodiments, the immunogenic composition further comprises at least one additional tumor-associated antigen, wherein the at least one additional tumor-associated antigen is exposed on the outer surface of the membrane vesicle. In further embodiments, the additional tumor-associated antigen is carbohydrate-based.

In some embodiments, the membrane vesicle is derived from a eukaryotic cell other than RBC (e.g. mesenchymal stem cells, platelets and cancer cells), wherein said membrane vesicle further comprises a coating material configured to prolong nanoparticle circulation, wherein the coating material is integrated in the outer surface of said membrane vesicle. An important but not-limiting example for a coating material configured to prolong circulation time is polyethylene glycol and derivatives thereof.

According to certain embodiment, the membrane vesicle further comprises a targeting agent conjugated to said membrane vesicle to direct the antigen to a particular in vivo location or particular cell population. According to certain embodiment, the membrane vesicle further comprises a targeting agent conjugated to the outer surface of the lipid bilayer of said membrane vesicle to direct the antigen to a particular in vivo location or particular cell population.

According to additional embodiments, the immunogenic composition may further comprise an adjuvant approved for human use in order to enhance immune reactions.

According to some aspects and embodiments, the present invention provides a vaccine composition comprising the immunogenic composition as described in various embodiments above. In one embodiment, the present invention provides a vaccine for use in treating cancer, wherein the cancer is Neu5Gc-positive.

As used herein, the term "vaccine" refers to a therapeutic vaccine or more specifically to a therapeutic anti-cancer vaccine, and means a composition that can be administered to an individual already diagnosed with cancer disease in order to eradicate cancer cells through strengthening patient's own immune response. The immune response can reduce tumor growth and/or prevent or delay tumor recurrence upon partial or complete remission of the cancer.

It will, of course, be appreciated that the vaccine composition of this invention may comprise as additional ingredients any of the conventional vaccine additives, such as sodium chloride, phosphates and preservatives.

The vaccine composition can be administered to an individual in a regimen determined as appropriate by a person skilled in the art. For example, the composition may be given multiple times at an appropriate interval and dosage.

In some embodiments, the vaccine composition is frozen-thawed. In some embodiments, the immunogenic composition is frozen-thawed. In some embodiments, the immunogenic composition undergoes a freeze-thaw cycle before use. In some embodiments, membrane vesicles bearing Neu5Gc glycoconjugates that have undergone a freeze-thaw cycle, preserve their immunogenicity.

As used herein, the term "freeze-thaw cycle" refers to freezing the immunogenic composition or the membrane vesicles to a temperature below 0° C., maintaining the immunogenic composition or the membrane vesicles in a temperature below 0° C. for a defined period of time and thawing the immunogenic composition or the membrane vesicles to room temperature or body temperature or any temperature above 0° C. Each possibility represents a separate embodiment of the present invention. The term "room temperature", as used herein typically refers to a temperature of between 18° C. and 25° C. The term "body temperature", as used herein, refers to a temperature of between 35.5° C. and 37.5° C., preferably 37° C.

The term "treating" is used herein to mean obtaining a desired pharmacological and/or physiological effect. The effect may be therapeutic in terms of partially or completely curing a disease and/or a symptom associated. The term "treating" as used herein covers any treatment of a disease in a subject and includes inhibiting the disease, i.e. arresting its development, or relieving the disease, i.e. causing regression of the disease.

According to some aspects, the present invention provides a method of using the vaccine for stimulating an anti-cancer immune response in a subject, comprising administration of the immunogenic composition to a subject. In some embodiments, the present invention provides a method of stimulating an anti-cancer immune response in a subject, the method comprising administering the vaccine composition of the invention. In certain embodiments, the subject is a mammal In some embodiments, the subject is a human. In further embodiments, the human is already diagnosed with Neu5Gc-positive cancer.

In some embodiments, the present invention provides a method of stimulating an anti-cancer immune response in a subject, the method comprising administering a vaccine composition to the subject, the vaccine composition comprising a plurality of membrane vesicles bearing Neu5Gc glycoconjugates, wherein the Neu5Gc glycoconjugates are exposed on the outer surface of the membrane vesicles, wherein said membrane vesicles are derived from the membrane of eukaryotic cells expressing Neu5Gc, wherein the membrane vesicles have an average hydrodynamic diameter in the submicron range.

In some embodiments, the present invention provides an immunogenic composition for use in stimulating an anti-cancer immune response in a subject, the immunogenic composition comprises a therapeutically effective amount of the membrane vesicles of the invention in various embodiments thereof. In some embodiments, the present invention provides an immunogenic composition for use in stimulating an anti-cancer immune response in a subject, the immunogenic composition comprises a plurality of membrane vesicles bearing Neu5Gc glycoconjugates, wherein the Neu5Gc glycoconjugates are exposed on the surface of the membrane vesicles, wherein said membrane vesicles are derived from the membrane of eukaryotic cells expressing Neu5Gc, wherein the membrane vesicles have an average hydrodynamic diameter in the submicron range.

In various embodiments, the vaccine composition is administered by a method selected from the group consisting but not limited to oral administration, subcutaneous administration, aerosol administration, intraperitoneal injection, intravenous injection and intramuscular injection. Each possibility represents a separate embodiment of the present invention. In further embodiments, the vaccine composition is administered by a method selected from the group consisting of intravenous injection and intramuscular injection. In further embodiments, the vaccine composition is administered by intravenous injection.

Active vaccination can induce a sustained and broad immune response, given selection of various factors, including number of exposures and intervals between exposures. In some embodiments, the method of using the vaccine comprises a single administration. In some embodiments, the method of using the vaccine comprises repeated administrations to enhance the treatment efficacy. In some embodiments, the method of stimulating an anti-cancer immune response in a subject comprises repeated administrations to enhance the treatment efficacy.

In some embodiments, the method of using the vaccine further comprises administering at least one additional immunotherapeutic drug. In some embodiments, the method of stimulating an anti-cancer immune response in a subject further comprises administering at least one additional immunotherapeutic drug. In some embodiments, the vaccine composition and the at least one additional immunotherapeutic drug are administered substantially simultaneously, concurrently, alternately, successively or according to overlapping schedules. Each possibility represents a separate embodiment of the present invention.

In some embodiments, the at least one immunotherapeutic drug is an immune checkpoint inhibitor. In certain embodiments the immune checkpoint inhibitor is selected from PD-1 inhibitor, PD-L1 inhibitor and CTLA-4 inhibitor, or any other immune checkpoint inhibitor. Each possibility represents a separate embodiment of the present invention. In certain embodiments the immune checkpoint inhibitor is selected from PD-1 inhibitor and CTLA-4 inhibitor. In specific embodiments, the immune checkpoint inhibitor is a PD-1 inhibitor. In other embodiments, the immune checkpoint inhibitor is a CTLA-4 inhibitor.

In some embodiments, the method of using the vaccine further comprises administering at least one immune checkpoint inhibitor. In some embodiments, the method of stimulating an anti-cancer immune response in a subject further comprises administering at least one immune checkpoint inhibitor. In some embodiments, the method of using the vaccine further comprises administering at least two immune checkpoint inhibitors. In some embodiments, the method of stimulating an anti-cancer immune response in a subject further comprises administering at least two immune checkpoint inhibitors. In some embodiments, the method of using the vaccine further comprises administering two immune checkpoint inhibitors. In some embodiments, the two immune checkpoint inhibitors are PD-1 inhibitor and CTLA-4 inhibitor.

In some embodiments, the combination of the vaccine composition of the invention with the at least one immune checkpoint inhibitor/s leads to improved therapeutic efficacy than that of either treatment individually. In some embodiments, the combination of the vaccine composition of the invention with the at least one immune checkpoint inhibitor/s shows an additive or even a synergistic therapeutic effect. An additive effect is observed when the effect is equal to the sum of the individual effects of each treatment alone. A synergistic effect is observed when the effect is greater than the sum of the individual effects of the treatments. A synergistic effect is therefore greater than an additive effect. The therapeutic effect/efficacy of the treatments can be evaluated and compared by monitoring various parameters known in the art such as tumor growth inhibition. In some embodiments, the combination of the vaccine composition with the at least one immune checkpoint inhibitor/s leads to at least 5%, at least 10%, at least 15%, at least 20% at least 25%, at least 30%, at least 35%, at least 40%, at least 45%, at least 50%, at least 55%, or at least 60% improvement in the therapeutic efficacy of the vaccine composition.

As used herein, the term "plurality" includes two or more referents unless the content clearly dictates otherwise.

The terms "comprising", "comprise(s)", "include(s)", "having", "has" and "contain(s)," are used herein interchangeably and have the meaning of "consisting at least in part of". When interpreting each statement in this specification that includes the term "comprising", features other than that or those prefaced by the term may also be present. Related terms such as "comprise" and "comprises" are to be interpreted in the same manner The terms "have", "has", having" and "comprising" may also encompass the meaning of "consisting of" and "consisting essentially of", and may be substituted by these terms. The term "consisting of" excludes any component, step or procedure not specifically delineated or listed. The term "consisting essentially of" means that the composition or component may include additional ingredients, but only if the additional ingredients do not materially alter the basic and novel characteristics of the claimed compositions or methods.

As used herein, the term "about", when referring to a measurable value such as an amount, a temporal duration, and the like, is meant to encompass variations of +/−10%, or +/−5%, +/−1%, or even +/−0.1% from the specified value.

As used herein and in the appended claims the singular forms "a", "an," and "the" include plural references unless the content clearly dictates otherwise. Thus, for example, reference to "the membrane vesicle" includes a plurality of such membrane vesicles, and so forth. It should be noted that the term "and" or the term "or" is generally employed in its sense including "and/or" unless the content clearly dictates otherwise.

The following examples are intended to illustrate how to make and use the compounds and methods of this invention and are in no way to be construed as a limitation. Although the invention will now be described in conjunction with specific embodiments thereof, it is evident that many modifications and variations will be apparent to those skilled in the art. Accordingly, it is intended to embrace all such modifications and variations that fall within the spirit and broad scope of the appended claims.

EXAMPLES

Materials and Methods

Materials

Dulbecco's Modified Eagle's Medium high Glucose (DMEM), Fetal Bovine Serum (FCS), L-Glutamine, Penicillin-streptomycin (pen-strep) Dulbecco's PBS were all purchased from biological industries; Trizma-hydrochloride, Tween-20, Ovalbumin (Grade V), O-phenylenediamine (OPD) and periodate were all purchased from Sigma-Aldrich, EDTA purchased from Fisher, Hydrogen peroxide 30% purchased from Merck.

Antibodies and Lectins

Chicken anti-Neu5Gc IgY (Biolegend), biotinylated-SNA, biotinylated-MALII (Vector Lab). HRP-donkey-anti-chicken IgY, HRP-Streptavidin, Cy3-goat-anti-mouse IgG, Cy3-goat-anti-mouse IgM, Cy3-donkey-anti-chicken IgY and Cy3-Strepavidin (Jackson ImmunoResearch).

Cell Lines and Mice

MC38-GFP cells (murine colon adenocarcinoma cells stably expressing GFP) were grown in culture (DMEM with high glucose, 10% FCS, 1% Glutamine, 1% pen-strep). $Cmah^{-/-}$ mice were bred and maintained according to Animal Care and Use Committee protocol approved by Tel Aviv university.

Generation of Nano-Ghost (NG) Glyconanoparticles from Porcine Red Blood Cells

Nano-ghost (NG) were prepared from porcine red blood cells (RBCs) of two strains: α-Gal $Ggta1^{-/-}$ knocked-out (Gal-KO; Neu5Gc-positive; $NG^{pos}$) and the double-KO $Ggta1^{-/-}/Cmah^{-/-}$ strain (Gal/Gc-DKO; Neu5Gc-Negative; $NG^{neg}$). RBCs were packed by 3 rounds of centrifugation in PBS pH 7.4 (1000×g, 10 min) then stored at −80° C. until used. Packed RBCs (2.5 ml) were lysed by incubation on ice with 25 ml ice cold lysis buffer (50 mM TRIS pH 7.35, 10 mM EDTA) for 10 min, then centrifuged for 30 min at 26,000×g with no brakes (to avoid pellet detachment). The supernatant was removed and lysis repeated until NG pellet was white. NG pellet was washed with 25 ml of ice-cold double distilled $H_2O$ (DDW), then re-suspended in 1 ml DDW. Protein content was determined by BCA (Pierce), volume adjusted to a final concentration of 2 mg/ml, then 1 ml aliquots were stored at −80° C. until used. For physical characterization, NG were stored at 4° C. and analyzed within 24 hours of preparation.

Cryo Transmission Electron Microscopy (Cryo-TEM)

NG were diluted to 0.1 mg/ml and 5 μl were pipetted onto a plasma etched (25 s) 200 mesh holey carbon grid (PELCO) held in the plunge chamber at approximate 90% humidity. Sample preparation was carried out using a Cryo-Plunge 3 unit (Gatan Instruments) employing a double blot technique. The samples were blotted for 2 s, and then plunged into liquid ethane at a temperature of −170° C. After vitrification, the grids were transferred under liquid nitrogen to the cryo-TEM specimen holder (Gatan 626 cryo holder) at −170° C. Imaging was carried out using a Tecnai G2 cryo-TEM (FEI Company, Eindhoven, Netherlands) operated at 120 kV and imaged using a Gatan 4000 camera, and images were captured using a Digital Micrograph software (Gatan). During imaging, the temperature of the sample holder was maintained at −170° C. to inhibit sublimation of vitreous water.

Dynamic Light Scattering (DLS) Size and Zeta Potential

Freshly prepared NG were diluted in PBS pH 7.4 (for size) or water (for zeta potential) to 20 μg/ml total protein and measured in a Malvern Nano ZS zetasizer. Data calculations were performed with the Zetasizer software using the Intensity algorithm. Each experimental result is an average of at least 3 independent measurements. Error bars represent ±SD, with size SD calculated by multiplying the Mean Size with square root of the PDI (Poly dispersity index).

Protein Analysis of NG by Silver Staining

Freshly prepared NG were diluted in SDS sample buffer to 40 ng/μl, incubated at room temperature (RT) for 30 min, then separated on 12% SDS-PAGE gels. Gels were fixed for 20 min at RT in 25 ml fixation solution 1 (10% acetic acid, 40% ethanol, 50% DDW, 0.0185% Formaldehyde), then washed with 50% Ethanol for 10 min 3 times, sensitized for 1 min with 25 ml 0.02% $Na_2S_2O_3$ in DDW, washed with water for 20 sec 3 times, then incubated for 12 minutes with 25 ml Silver Nitrate solution (9.4 mM $AgNO_4$ containing 0.02% formaldehyde), and washed with water for 20 sec 3 times. Gels were developed with Developing Solution (0.0005% $Na_2S_2O_3$, 0.015% formaldehyde, 5% $Na_2CO_3$) until bands appear then stopped with fixation solution 2 (10% acetic acid, 40% ethanol, 50% DDW), then gels were scanned.

Sialic Acid Analysis of NG by Western Blotting

Sialic acid content was defined using lectin analysis by Western blotting. Freshly prepared NG were diluted in SDS sample buffer to 40 ng/μl, incubated at room temperature for 30 min, then separated on 12% SDS-PAGE gels, followed by transfer onto nitrocellulose membrane (Whatman, GE life technologies). Membranes were blocked with TBST (50 mM Tris pH 7.6, 0.15 M NaCl, 0.1 Tween-20) supplemented with 2% fish gelatin (Sigma) for 1 hour at RT with gentle shaking, then washed 3 times with TBST and incubated with primary detection for 1 hour at RT (chicken anti-Neu5Gc IgY diluted 1:1000 or biotinylated lectins; Bio-SNA diluted to 0.4 μg/ml and Bio-MALII diluted to 4 μg/ml). Next, membranes were washed 3 times with TBST and incubated with secondary detection for 1 hour at RT (HRP-donkey-anti-chicken IgY 0.16 μg/ml or HRP-Streptavidin 0.1 μg/ml, respectively). Membranes were developed using an enhanced chemiluminescence kit (ECL; Pierce).

Sialic Acid Specificity Analysis by Mild Periodate Oxidation Treatment

Freshly prepared NG were diluted in SDS sample buffer to 40 ng/μl and incubated at room temperature for 30 min. The samples were separated on 12% SDS-PAGE gels, followed by transfer onto nitrocellulose membrane (Whatman, GE life technologies). Membranes were washed 3 times with ice cold water, then with ice cold PBS pH 6.5 (8.7 mM $NaH_2PO_4$, 137 mM NaCl), then incubated with 2 mM Periodate diluted in PBS 6.5 for 30 minutes, protected from light, at RT. Then membranes were washed 6 times with water and further analyzed by Western blotting, as described.

Sialic Acid Analysis by Lectin ELISA

NG were coated in duplicates at 1 μg protein/well in 50 mM sodium carbonate-bicarbonate buffer, pH 9.5 onto 96-well microtiter plates (Costar, Corning) then incubated overnight at 4° C. Wells were blocked for 1 hour at RT with blocking buffer (PBS pH 7.4, 1% ovalbumin), then aspirated and incubated with diluted primary antibody at 100 μl/well in the same blocking buffer for two hours at RT (chicken anti-Neu5Gc IgY at 1:1000, biotinylated SNA or MAL-II at 1 μg/ml). Plates were washed three times with PBST (PBS pH 7.4, 0.1% Tween-20) then incubated for 1 hour at RT with HRP-conjugated secondary antibody in PBS (HRP-donkey-anti-chicken IgY 0.26 μg/ml or HRP-streptavidin 0.1 μg/ml, respectively). After washing three times with PBST, wells were developed with 140 μl of O-phenylenediamine in 100 mM citrate-$PO_4$ buffer, pH 5.5, and the reaction stopped with 40 μl of $H_2SO_4$ (4 M). Absorbance was measured at 490 nm on SpectraMax M3 (Molecular Devices). Specific binding was defined by subtracting the background readings obtained with the secondary antibody only on coated wells.

Sialoglycan Microarray Fabrication

Arrays were printed as described (Leviatan, S. Ben-Arye, et al., Journal of visualized experiments: JoVE, 2017, 125). Arrays were fabricated with NanoPrint LM-60 Microarray Printer (Arrayit, CA) on epoxide-derivatized slides (Corning) with 16 sub-array blocks on each slide. Glycoconjugates were distributed into one 384-well source plates using 4 replicate wells per sample and 8 μl per well (Version 1.0). Each glycoconjugate was prepared at 100 μM in an optimized print buffer (300 mM phosphate buffer, pH 8.4). To monitor printing quality, replicate-wells of mouse IgG (Jackson ImmunoResearch, at 200, 100, 50, 25, 12.5, 6.25 ng/μl in PBS+10% glycerol) and AlexaFlour-555-Hydraside (Invitrogen, at 1 ng/μl in 178 mM phosphate buffer, pH 5.5) were used for each printing run. The arrays were printed with four SMP3 pins (5 μm tip, 0.25 μl sample channel, ~100 μm spot diameter; Arrayit, CA). Each block (sub-array) has 17 spots/row, 20 columns with spot-to-spot spacing of 225 μm. The humidity level in the arraying chamber was maintained at about 66% during printing. Printed slides were left on arrayer deck over-night, allowing humidity to drop to ambient levels (40-45%). Next, slides were packed, vacuum-sealed and stored in a desiccant chamber at RT until used. Slides were printed in one batch of 56 slides.

NG Stability Analysis Using Microarray

Arrays were printed with NanoPrint LM-60 Microarray Printer (Arrayit, CA) on epoxide-derivatized slides (Corning) with 16 sub-array blocks on each slide. Glycoconjugates and freshly prepared NG diluted to 40 ng/μl in 187 mM Phosphate Buffer pH 8.4 were distributed into one 384-well source plates using 4 replicate wells per sample and 8 μl per well. In addition, in order to investigate the stability of NG, 40 μl from each NG preparation were frozen 5 minutes in −80° C., quickly thawed and diluted to 40 ng/μl. This cycle was repeated twice and the diluted samples were printed as well. Synthetic glycans were also printed and diluted to 100 μM in 300 mM phosphate buffer, pH 8.4. To monitor printing quality, AlexaFlour-555-Hydraside (Invitrogen, at 1 ng/μl in 178 mM phosphate buffer, pH 5.5) was used for each printing run. The arrays were printed with 4 SMP3 pin (5 μm tip, 0.25 μl sample channel, ~100 μm spot diameter; Arrayit, CA). Each block (sub-array) has 16 rows, 10 columns with spot-to-spot spacing of 225 μm. The humidity level in the arraying chamber was maintained at about 70% during printing. Printed slides were left on arrayer deck over-night, allowing humidity to drop to ambient levels (40-45%). Next, slides were packed, vacuum-sealed and stored in a desiccant chamber at RT until used. Slides were developed using antibodies as described.

Evaluating Anti-NG Response in Immunized Mice Using Microarray

Arrays were printed with NanoPrint LM-60 Microarray Printer (Arrayit, CA) on epoxide-derivatized slides (Corning) with 16 sub-array blocks on each slide. NG as well as synthetic glycans were distributed into one 384-well source plates using 4 replicate wells per sample and 8 μl per well. Each NG sample was diluted in PBS pH 7.4 to 100 ng/μl and Synthetic glycans at 100 μM in 300 mM phosphate buffer, pH 8.4. To monitor printing quality, mouse IgG (Jackson ImmunoResearch) at 40 ng/μl in PBS+10% glycerol and AlexaFlour-555-Hydraside (Invitrogen, at 1 ng/μl in 178 mM phosphate buffer, pH 5.5) were used for each printing run. The arrays were printed with one SMP3 pin (5 μm tip, 0.25 μl sample channel, ~100 μm spot diameter; Arrayit, CA). Each block (sub-array) had 14 rows, 6 columns with spot-to-spot spacing of 225 μm. The humidity level in the arraying chamber was maintained at about 70% during printing. Printed slides were left on arrayer deck over-night, allowing humidity to drop to ambient levels (40-45%). Next, slides were packed, vacuum-sealed and stored in a desiccant chamber at RT until used. Slides were developed using antibodies as described.

Glycan Microarray Binding Assay

Slides were developed and analyzed as previously described (Leviatan, S. Ben-Arye, et al., Journal of visualized experiments: JoVE, 2017, 125). Slides were rehydrated with $dH_2O$ and incubated for 30 min in a staining dish with 50° C. pre-warmed 0.05 M ethanolamine in 0.1 M Tris, pH 9.0 to block the remaining reactive epoxy groups on the slide surface, then washed with 50° C. pre-warmed $dH_2O$. Slides were centrifuged at 200×g for 3 min, then fitted with ProPlate™ Multi-Array 16-well slide module (Invitrogen) to divide into the 16 sub-arrays (blocks). Slides were washed with PBST (PBS pH 7.4, 0.1% Tween-20), aspirated and blocked with 200 μl/sub-array of blocking buffer (PBS/OVA; PBS pH 7.4, 1% ovalbumin) for 1 hour at RT with gentle shaking. Next, the blocking solution was aspirated and 100 μl/block of primary detection diluted in PBS/OVA was added; mice sera (1/100) or chicken anti-Neu5Gc IgY (1/7000), or Bio-SNA (10 ng/μl). Primary detections were incubated with gentle shaking for 2 hours at RT. Slides were washed three times with PBST then with PBS for 5 min/wash with shaking. Bound antibodies were detected by incubating with secondary detection diluted in PBS, 200

μl/block at RT for 1 hour: Cy3-goat-anti-mouse IgG (1.5 μg/ml) or Cy3-donkey-anti-chicken IgY (0.375 μg/ml) or Cy3-Streptavidin (1.2 μg/ml). Slides were washed three times with PBST then with PBS for 5 min/wash followed by removal from ProPlate™ Multi-Array slide module and immediately dipping slide in a staining dish with $dH_2O$ for 10 min with shaking, then centrifuged at 200×g for 5 min. Dry slides were vacuum-sealed and stored in dark until scanning.

Array Slide Processing

Processed slides were scanned and analyzed as described (Leviatan, S. Ben-Arye, et at, Journal of visualized experiments: JoVE, 2017, 125) at 10 μm resolution with a Genepix 4000B microarray scanner (Molecular Devices) using 350 gain. Images were analyzed by Genepix Pro 6.0 software (Molecular Devices). Spots were defined as circular features with a variable radius and local background subtraction was performed. Data was analyzed by Excel.

Cancer Vaccine Mouse Immunization Protocol

Figure 4A:
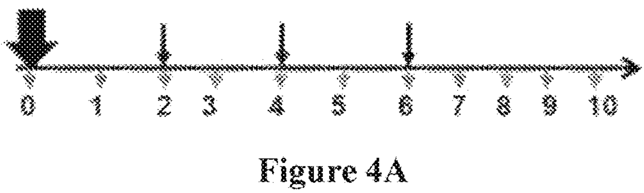
FIGS. 4A-4G demonstrate the serum antibodies response during treatment according to additional vaccination regimes.

All animal experiments were conducted according to the guidelines of the Tel-Aviv University Institutional Animal Care and Use Committee. 6-10 weeks old $Cmah^{-/-}$ mice were i.p. immunized with either $NG^{pod}$ or $NG^{neg}$. NG at 2 mg/ml protein concentration were mixed 1:1 with Freud's complete adjuvant (FCA) or Freud's incomplete adjuvant (FIA) until emulsified, then 200 μl were used for i.p injections (100 μg NG/mouse). In the first immunization protocol (B2W; n=10), FCA i.p. immunization at week 0 was followed by three boost immunizations with FIA at two-week intervals (weeks 2, 4, 6; FIG. 4A). In the second immunization protocol (B1W; n=10), FCA i.p. immunization at week 0 was followed by two boost immunizations with FIA at one-week intervals (weeks 2, 4), followed by another boost at week 6 (FIG. 4A). To evaluate the developed anti-Neu5Gc antibodies response and kinetics, mice were bled (facial vein) on a weekly basis, blood incubated overnight at 4° C., then centrifuged at 17,000×g for 2 min and serum collected. Samples were stored at −80° C. until analyzed by glycan microarray.

To evaluate the significance of Freund's adjuvant for the development of IgG antibodies, mice were immunized according to B2W protocol with either $NG^{pos}$ or $NG^{neg}$ in FCA/FIA (n=7 per group) or $NG^{pos}$ in PBS only (n=7). Serum was collected as described, before the first injection and 2 weeks after the second boost (at week 6).

Evaluating Cancer Vaccine Efficacy In Vivo

MC38-GFP cells (murine colon adenocarcinoma cells stably expressing GFP[90]) were grown in culture (DMEM with high glucose, 10% FCS, 1% Glutamine, 1% pen-strep) to 80% confluence, lifted with PBS/EDTA (10 mM EDTA in PBS without $Ca^{+2}/Mg^{+2}$) then centrifuged 1500×g for 5 min at 4° C. and resuspended in DPBS. At week 7.5 after cancer vaccine ($NG^{pos}$) or control immunization ($NG^{neg}$), at either B2W or B1W protocols, $Cmah^{-/-}$ mice were subcutaneously injected at the flank with $0.5\times10^6$ cells/mouse in 150 μl DPBS. Tumors were palpable 5 days later, then tumors measured every other day using a digital caliper and tumor volume calculated [(height×length×width)/2].

To evaluate the effect of low levels anti-Neu5Gc antibodies on tumor progression, $Cmah^{-/-}$ mice were immunized with either cancer vaccine ($NG^{pos}$) or control immunization ($NG^{neg}$) using the B2W protocol with only 2 FIA boost immunizations (weeks 2 and 4), and one week later (week 5) mice were inoculated with $0.5\times10^6$ MC38-GFP cells/mouse, then monitored as described above.

Preparation Intra-Tumoral IgG

Tumors from cancer vaccine or control treated mice were harvested on day 21, sliced to small pieces (~2 mm) and incubated in DMEM with collagenase type II (1 mg/ml) and DNAse-I (0.5 mg/ml) for 30 minutes at 37° C. (total volume of 3.5 ml/sample). The suspension was centrifuged for 10 minutes at 400×g and the supernatant collected, then again centrifuged at 400×g for 5 min. Resulting supernatants were transferred to 15 ml tubes, and 50 μl of pre-washed protein A Sepharose 4 Fast Flow beads (GE Healthcare) were added to each tube. Samples were incubated for 48 hours at 4° C. while mixing, then loaded on a polyprep column (BioRad), washed 3 times with PBS, then eluted with 0.5 ml 0.1 M Glycine, pH 2.5 into tubes containing 120 μl 1M Tris, pH 9. Purified IgG antibodies were stored at 4° C. until analyzed by glycan microarray.

Examining Efficacy of Combination Therapy of Active Cancer Vaccine with Checkpoint Inhibitors Nano-Ghost (NG) vaccine mouse immunization protocol: 6-10 weeks old $Cmah^{-/-}$ mice are i.p. immunized with either $NGP^{pos}$ or $NG^{neg}$. NG at 2 mg/ml protein concentration are mixed 1:1 with FCA until emulsified. 200 μl are injected i.p (100 μg NG/mouse) at week 0. At week 1, 2 and 6, three more boosts are given, mixed 1:1 with FIA. To evaluate the developed anti-Neu5Gc antibodies response and kinetics, mice are bled (facial vein) on a weekly basis, blood is incubated at room temperature for 2 hours, then centrifuged at 14,000×g for 3 min and serum is collected.

Checkpoint inhibitors blockade: Mice are injected i.p. with immune checkpoint inhibitors on days 4, 8, 14, and 18 after tumor inoculation, 200 μl/mice diluted in PBS: anti-mouse PD-1 RMP1-14, (200 mg/ml) together with anti-mouse CTLA-4 (CD152) Clone: 9D9 (100 mg/ml).

Antibodies: For Array: Cy3-goat-anti-mouse IgG; For FACS: PE/Dazzle-594 Rat anti-mouse CD25, BV-510 Rat anti-mouse CD8a PE/Cy5 Rat anti-mouse F4/80, APC/Cy7 Rat anti-mouse CD4, PerCP Armenian hamster anti-mouse CD11c, Pacific blue Rat anti-mouse CD45, PE/Cy 7 Rat anti-mouse LY6c, BV 650 Rat anti-mouse/human CD11b, PE Armenian hamster anti-mouse CD196, Zombie Yellow™ Fixable Viability Kit, FC-R Leaf purified anti-CD16/32, APC-Rat anti-mouse CD3; For Immunization: Rat anti-mouse PD-1, RMP1-14, Mouse anti-mouse CTLA-4 (CD152) Clone: 9D9.

Single cell suspension: Tumors from NG cancer vaccine or control treated mice are harvested on day 20 (or day 21), sliced into small pieces (~2 mm) and incubated in DMEM with collagenase type II (1 mg/ml) and DNAse-I (0.5 mg/ml) for 15 minutes at 37° C. (total volume of 3.5 ml/sample). The suspension is centrifuged for 5 minutes at 400×g and the supernatant is collected.

Purification of intra-tumoral IgG: After single cell suspension the supernatants of the tumor samples are transferred to 15 ml tubes, and 50 μl of pre-washed protein A-Sepharose 4 Fast Flow beads (GE Healthcare) are added to each tube. Samples are incubated for 48 hours at 4° C. while mixing, then loaded on a polyprep column (BioRad), washed 3 times with PBS, then eluted with 0.5 ml 0.1 M Glycine, pH 2.5 into tubes containing 120 μl 1M Tris, pH-9, glycerol 1:1 is added to the samples. Purified IgG antibodies are stored at −20° C. until analyzed by glycan microarray.

RNA isolation: After tumor cell suspension, the solution is centrifuged for 5 minutes at 400×g and the pellet is re-suspended in PBS+5 mM EDTA. Then the samples are divided into tumor cells and immune cells by FACS sorter, according to GFP label (tumor cells GFP positive). Next, RNA isolation is performed with RNeasy Micro Kit (QIAGEN), RNA samples are estimated by nanodrop device and stored in −80° C.

FACS analysis peripheral blood mononuclear cells (PBMCs) and tumor cells: PBMCs from mice blood are collected into EDTA coated tube containing extra 10 μl of 0.17M EDTA. Samples are slowly swirled few times to avoid clumps, then the blood is diluted with RPMI medium (1:4 ratio, blood:RPMI). Ficoll-Paque media is added to FACS centrifuge tube and diluted blood sample carefully layered onto the Ficoll-Paque media solution (3:4 Ficoll: blood ratio). Samples are centrifuged (400×g, 30 min, 20° C., brake off) and the upper layer are discarded leaving the PBMCs. Then, PBMCs are washed with PBS and centrifuged (500×g, 5 min, 4° C.). $10^6$ cells are stained as mention bellow.

MC38-GFP tumors are collected on day 20 (or day 21 as indicated), tumor cell suspension is performed, the suspension is centrifuged for 5 min at 400 g and resuspended in PBS+5 mM EDTA. Samples are centrifuged (500×g, 5 min, 4° C.) and $10^6$ cells are stained as mention bellow.

Cell staining: Zombie Yellow™ Fixable Viability Kit added (1:1000) and incubated for 15 min RT covered with foil, then washed with PBS and centrifuged (500×g, 5 min, 4° C.). FC blocker—CD16/32 is added, diluted in FACS Buffer (PBS+0.5% fish gelatin) and incubated on ice for 10 min covered with foil, then washed. Cocktail of antibodies is added: CD8a (2.5 μg per $1\times10^6$ cells in 100 μl), CD11b (1.5 μg per $1\times10^6$ cells in 100 μl), CD25 (2.5 μg per $1\times10^6$ cells in 100 μl), Ly6c (0.3 μg per $1\times10^6$ cells in 100 μl), CD4 (5 μg per $1\times10^6$ cells in 100 μl), CD45 (0.5 μg per $1\times10^6$ cells in 100 μl), F4/80 (5 μg per $1\times10^6$ cells in 100 μl), CD196 (1.25 μg per $1\times10^6$ cells in 100 μl), CD11C (1.25 μg per $1\times10^6$ cells in 100 μl), CD3 (1 μg per $1\times10^6$ cells in 100 μl), incubated for 30 min on ice covered with foil and then washed. FACS buffer is added and samples are read by CytoFLEX flow cytometry device. The analysis is performed with Kaluza 2.0 program.

Statistical Analysis

One-way or Two-way analysis of variance (ANOVA) test for multiple comparison, or t-test, were performed using Graphpad Prism software (version 6). The significance level was defined as p>0.05. The results were expressed as mean±STD or SEM.

Example 1

Generation and Characterization of Biomimetic Glyconanoparticles

To generate biomimetic glyconanoparticles that express Neu5Gc-TACA in their natural context, porcine-derived RBCs that naturally express Neu5Gc-glycoconjugates were used. However, porcine also express the carbohydrate aGal (Galα1-3Galβ1-4GlcNAc-R) that is an immunogenic xeno-antigen in humans, and against which all humans have circulating anti-Gal antibodies. To eliminate the αGal antigen, a porcine strain that is deficient in the GGTA1 gene encoding the α1,3-galactosyltransferase (α1,3GT) was used. Thus, RBCs from two porcine knockout strains were used, that express either Neu5Gc-glycoconjugates (Neu5Gc$^{pos}$; Ggta1$^{-/-}$ knocked-out strain; Gal-KO), or control glycoconjugates that lack Neu5Gc, but instead express the non-immunogenic Neu5Ac (Neu5Gc$^{neg}$; double-knocked-out Ggta1$^{-/-}$/Cmah$^{-/-}$ strain; Gal/Gc-DKO). The chemical structures of Neu5Gc and Neu5Ac are presented in FIG. 1A. RBCs were first purified from fresh blood of these porcine knockout strains by centrifugation and PBS wash. Then isolated RBCs went through membrane rupture in a hypotonic buffer to remove the intracellular contents. Next, the emptied RBCs were washed, then resuspended to create glycoproteolipid nano-ghost vesicles (NG).

Figure 1G:
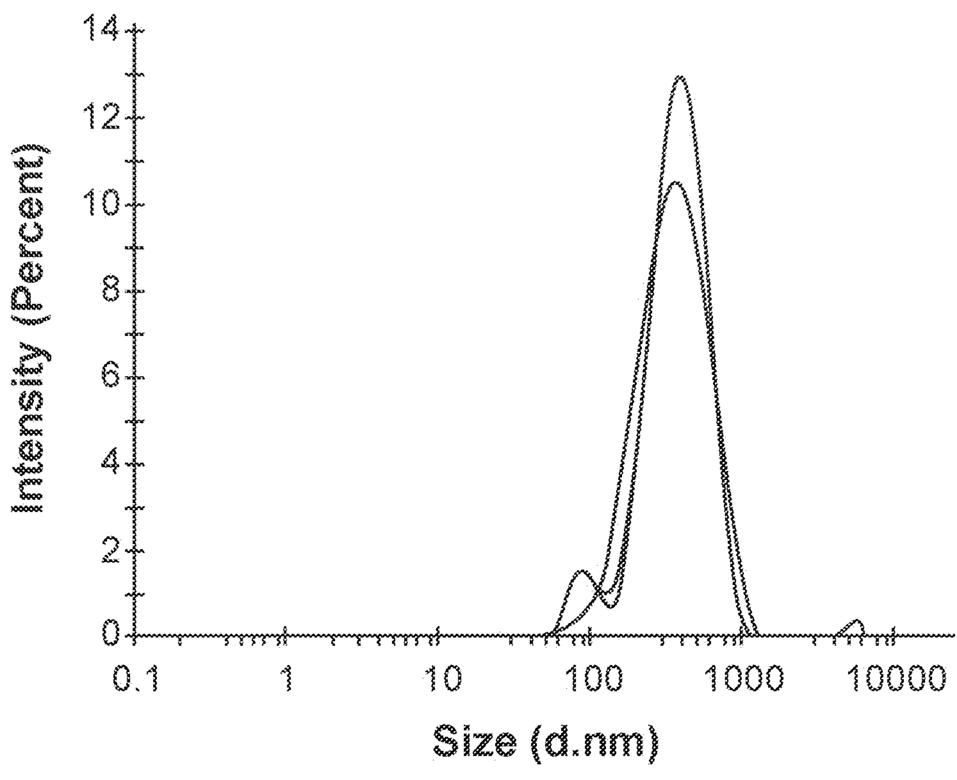

The physiochemical properties of these NG biomimetic glyconanoparticles were examined by Cryo transmission electron microscopy (cryo-TEM), showing a similar and uniform morphology of NG that either express Neu5Gc (Neu5Gc$^{pos}$-NG; NG$^{pos}$) or lack its expression (Neu5Gc$^{neg}$-NG; NG$^{neg}$) (FIG. 1B and FIG. 1C). Zeta potential measurements and dynamic light scattering (DLS) analysis indicated that both NG$^{pos}$/NG$^{neg}$ had a similar zeta potential of approximately −25 mV (FIG. 1D), and an average hydrodynamic diameter of ~400 nm (FIG. 1E, FIG. 1F, and FIG. 1G).

Figure 2A:
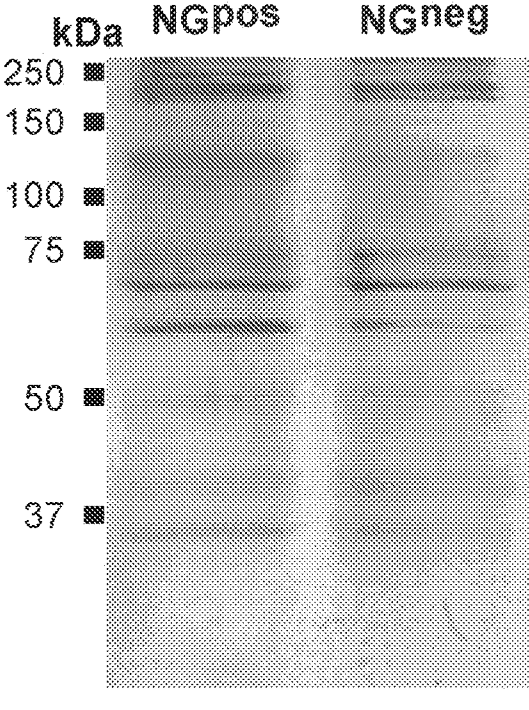
FIGS. 2A-2D present Biochemical characterization of $NG^{pos}$ and $NG^{neg}$.
Figure 2B:
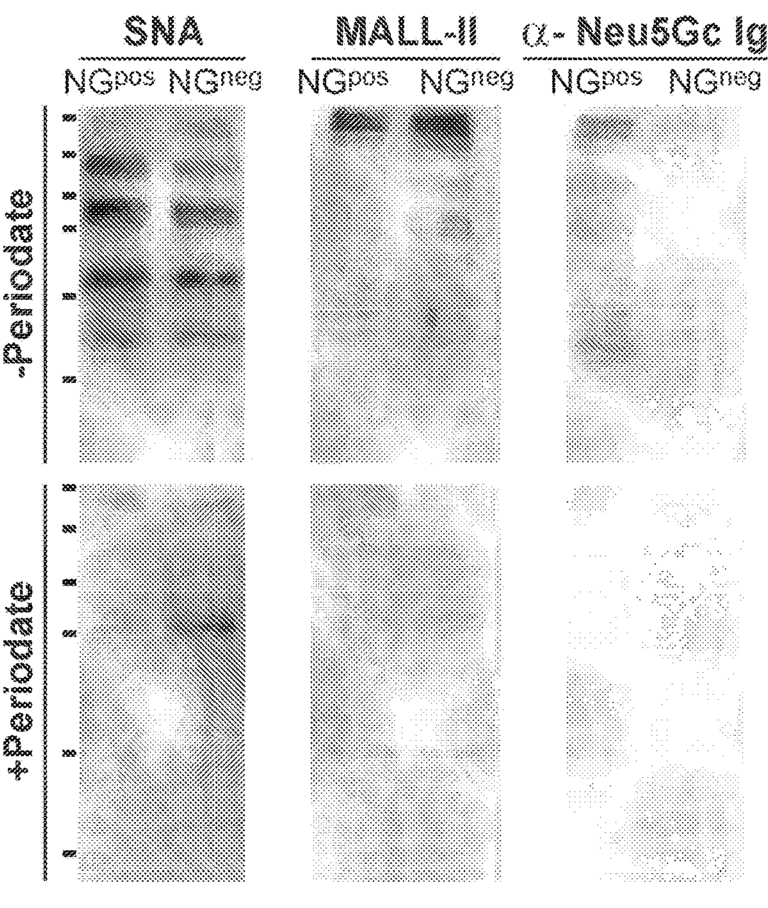

Further biochemical characterization demonstrated similar protein content by silver staining (FIG. 2A), containing all expected major RBC membrane protein bands. Subsequently, the sialic acid (Sia) content was compared between the two NG preparations by Western blot developed with the Sia-binding proteins: Sambucus Nigra Agglutinin (SNA) lectin that binds Siaα2-6-linked, Maackia Amurensis Lectin II (MAL-II) that binds Siaα2-3-linked, and the polyclonal chicken-anti-Neu5Gc IgY that bind various Neu5Gc-containing glycans (FIG. 2B). Sia-specific binding was confirmed by mild-periodate oxidation treatment that truncates two carbons off the Sia side chain, hence resulting in loss of Sia-binding. This biochemical analysis revealed that parallel glycoproteins bands were stained with both SNA and MAL-II lectins, demonstrating both terminal Siaα2-6 and Siaα2-3, and supporting a similar Sia content in both NG$^{pos}$/NG$^{neg}$ (FIG. 2B). Importantly, the Sia staining was mostly removed with periodate oxidation hence confirming Sia-specific recognition. In addition, Neu5Gc was only present in NG$^{pos}$ but not in NG$^{neg}$, and its staining was eliminated after treatment with periodate (FIG. 2B). Taken together, these results indicate that the only difference between NG$^{pos}$/NG$^{neg}$ preparations is the presence or lack of Neu5Gc expression, respectively. In fact, NG$^{pos}$ contain diverse Neu5Gc-glycans, while NG$^{neg}$ contain diverse Neu5Ac-glycans. Of note, the glycans on these two NG preparations differ only by the additional hydroxyl group in glycans covered with Neu5Gc instead of Neu5Ac.

Figure 2C:
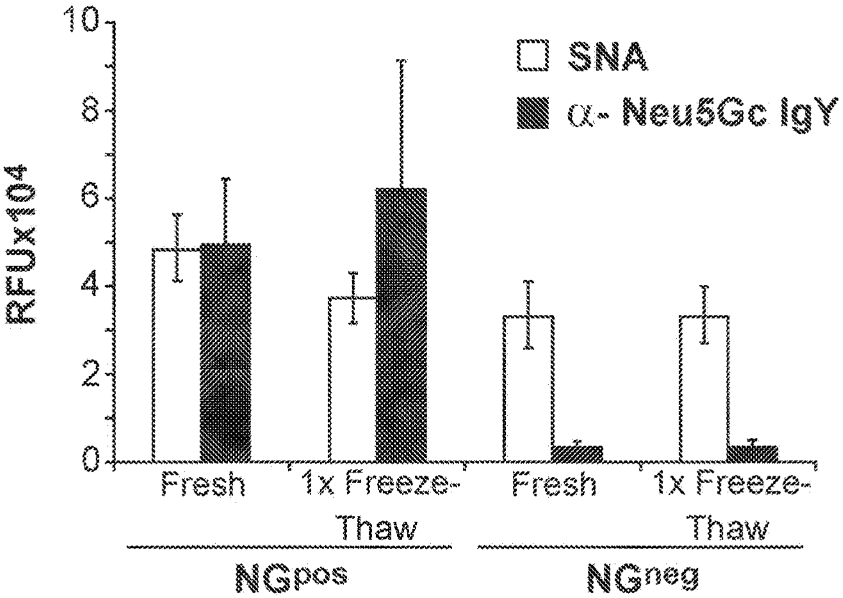
Figure 2D:
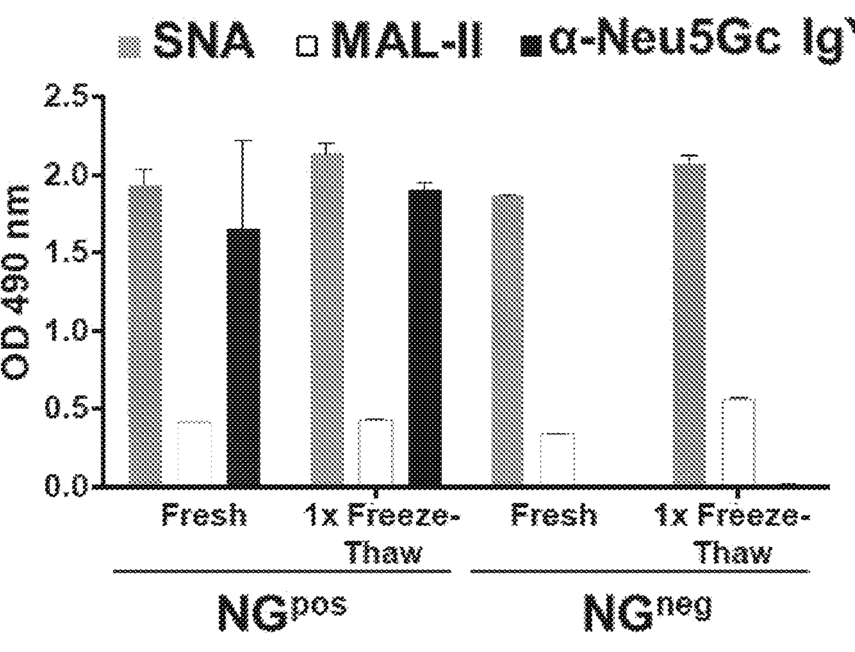

Once prepared, the NG were kept frozen at −80° C. until further use. To monitor the stability of NG after several freeze-thaw cycles, NG were printed onto epoxide-activated glass slides using a nano-printer, then slides developed with Sia-binding proteins. This indicated that Sia content had not changed after one freeze-thaw cycle (FIG. 2C). However, SNA and anti-Neu5Gc IgY reactivity had been reduced at the second and third freeze-thaw cycles. This is likely due to NG degradation or inside-out flipping, both resulting in reduced expression of sialylated-antigens Similar results were obtained when freshly-prepared, or once-thawed NG, were coated onto ELISA plate and examined with SNA, MAL-II and anti-Neu5Gc IgY, demonstrating stable reactivity after one freeze-thaw cycle (FIG. 2D). Therefore, all NG preparations had been aliquoted and used fresh or after only one freeze-thaw cycle in all subsequent studies.

Example 2

NG Vaccination for Sustained and Robust Anti-Neu5Gc Immune Response

Figure 3A:
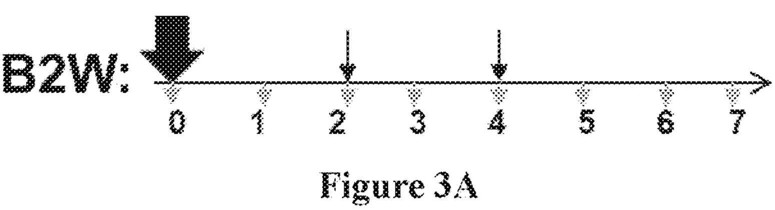
FIGS. 3A-3C demonstrate the serum antibodies response during treatment according to the initial vaccination regime.
Figure 3B:
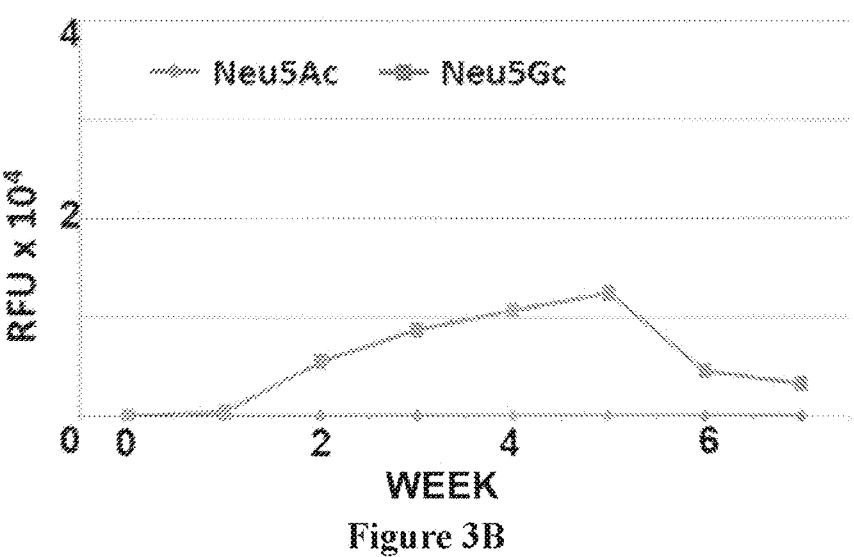
Figure 3C:
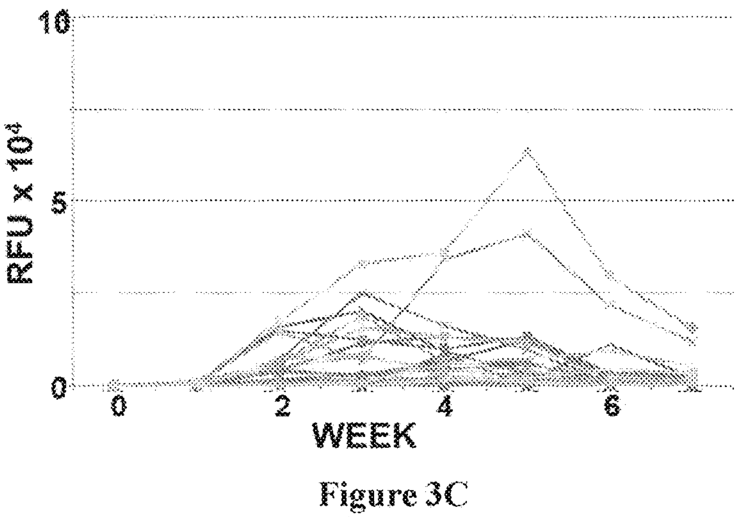
Figure 4B:
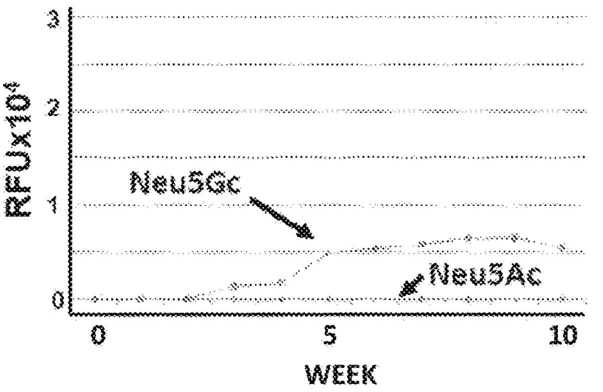
Figure 4C:
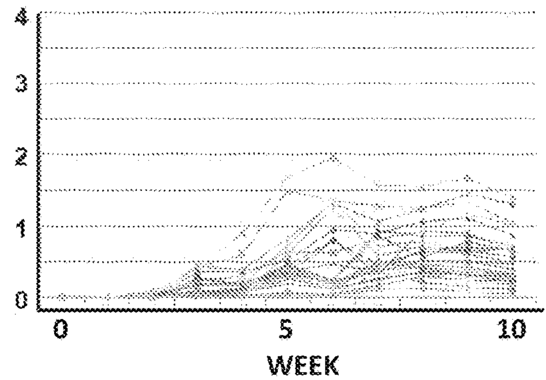
Figure 4D:
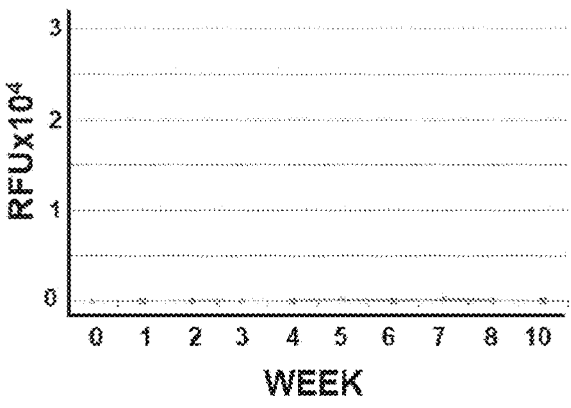

To determine the immunization protocol for sustained anti-Neu5Gc antibodies response, Cmah$^{-/-}$ mice were immunized with $NG^{pos}$ (Neu5Gc-glycans) or control $NG^{neg}$ (Neu5Ac-glycans) according to the vaccination regime presented in FIG. 3A (B2W). Mice were first immunized with $NG^{pos}$ or $NG^{neg}$ emulsified in Freund's Complete Adjuvant (FCA; FIG. 3A, thick black arrow), followed by two boost injections emulsified in Freund's Incomplete Adjuvant (FIA; FIG. 3A, thin black arrows), at two-week intervals (B2W). Mouse sera was collected weekly (FIG. 3A, grey arrows), then serum antibodies response was evaluated by sialoglycan microarrays printed with a diverse collection of Neu5Gc-glycans and Neu5Ac-glycans. This analysis showed an IgG response against only some of the Neu5Gc-glycans, which had dropped to baseline at week 6, two weeks after the second boost (FIG. 3B and FIG. 3C). Adding a third boost to the initial B2W regime at week 6 (FIG. 4A), slightly improved the diversity of anti-Neu5Gc IgG response, that was also sustained through week 10 (FIG. 4B and FIG. 4C). In both immunization protocols (B2W, 2 or 3 boosts) there was a complete absence of response against any of the Neu5Ac-glycans, that differ by only a single oxygen atom from their counterpart Neu5Gc-glycans (FIG. 3B and FIG. 4B) Similarly, immunization with the control $NG^{neg}$ (Neu5Ac-glycans) did not show any response against both Neu5Ac/Neu5Gc-glycans (FIG. 4D). These results exemplify the strong tolerance against the native Neu5Ac-glycans, in contrast to the high immunogenicity of Neu5Gc-glycans, and the resilient specificity of the developed immune response.

Figure 4E:
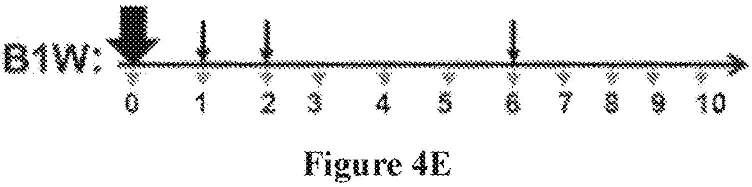
Figure 4F:
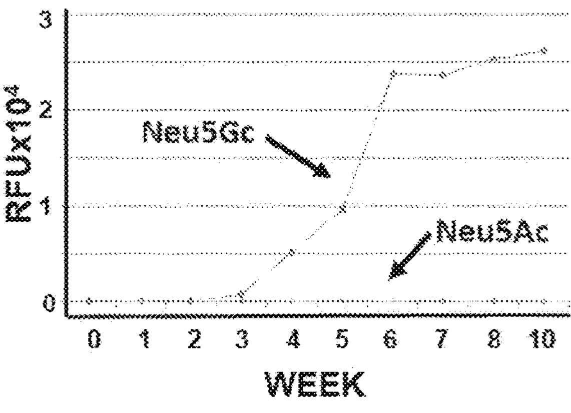
Figure 4G:
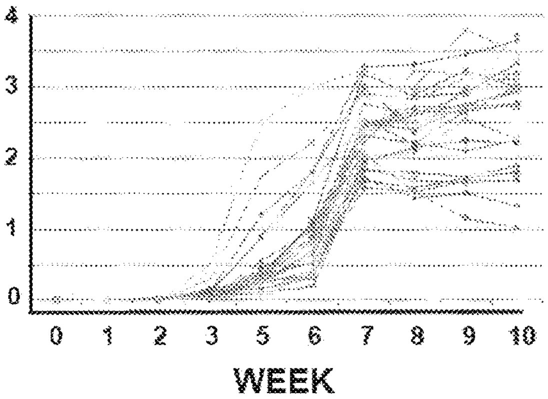
Figure 5:
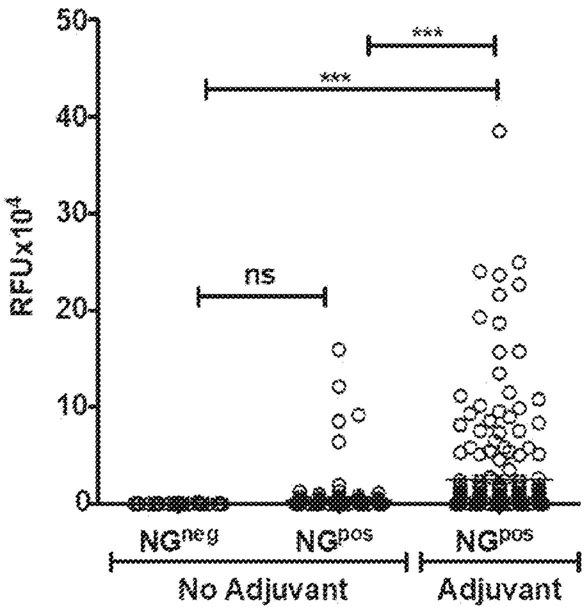
FIG. 5 presents statistical analysis of relative fluorescent units (RFU) obtained by sialoglycan microarray analysis of sera samples after injection of $NG^{pos}$ or $NG^{neg}$ with or without Freund's adjuvant, in the B2W regime.

To evaluate the contribution of the adjuvant to the developed response, $Cmah^{-/-}$ mice were immunized (B2W, 2 boosts) with $NG^{pos}$ or $NG^{neg}$, with or without adjuvant. Analysis of sera obtained at week 6 revealed a clear contribution of the adjuvant to the level and diversity of the developed anti-Neu5Gc IgG response (FIG. 5). Next, the interval between boost injections was further modified and persistence of response was evaluated. $Cmah^{-/-}$ mice were immunized with $NG^{pos}$ in FCA, then with two boost injections in FIA after one and two weeks, followed by a third boost 6 weeks after primary immunization (B1W regime; FIG. 4E). Glycan microarray analysis revealed a highly diverse, robust and persistent anti-Neu5Gc IgG response, that remained high even 10 weeks post primary immunization (FIG. 4F and FIG. 4G). Thus, B1W vaccination regime (weeks 0, 1, 2, 6) proved to be more efficient than B2W (weeks 0, 2, 4, 6), yielding a high and specific anti-Neu5Gc IgG response that was sustained for at least 4 weeks after the third boost.

Example 3

Evaluating Cancer Vaccine Efficacy Against Neu5Gc-Positive Tumors

Previous studies have shown that treatment of Neu5Gc-positive tumors with passively transferred anti-Neu5Gc antibodies in the Neu5Gc-deficient $Cmah^{-/-}$ mouse model have dualistic and opposing responses.

Figure 6A:
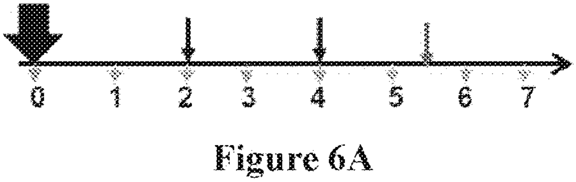
FIGS. 6A-6B show the evaluation of the effect of vaccine regime on tumor growth.
Figure 6B:
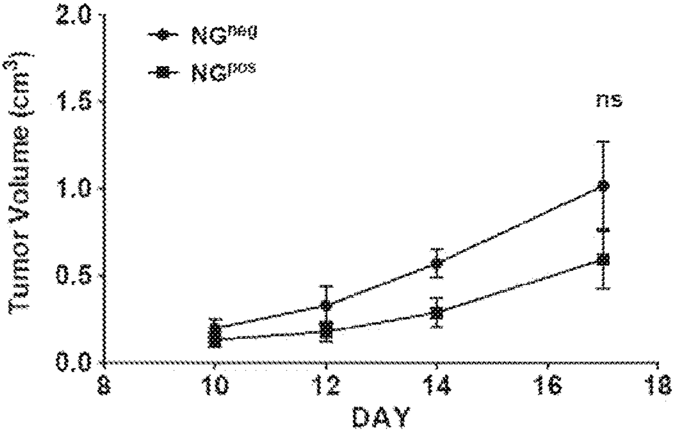

To evaluate safety of the active vaccine utilizing biomimetic glyconanoparticles, even at a low quality of response, mice were immunized with $NG^{pos}$ or $NG^{neg}$ at the non-optimal B2W regime (weeks 0, 2, 4; n=10 per group), then syngeneic Neu5Gc-positive tumors (mouse adenocarcinoma MC-38) inoculated subcutaneously at week 5.5 (FIG. 6A, upper grey arrow), and tumor growth was monitored. While $NG^{pos}$ vaccinated mice showed a slight decrease in tumor growth compared to $NG^{neg}$ group, this trend was not statistically significant (FIG. 6B). Nevertheless, unlike passive therapy, even at low quality of anti-Neu5Gc antibodies response (FIG. 3B), active vaccination did not mediate promotion of tumor growth, suggesting that the active vaccine is safe.

Figure 7A:
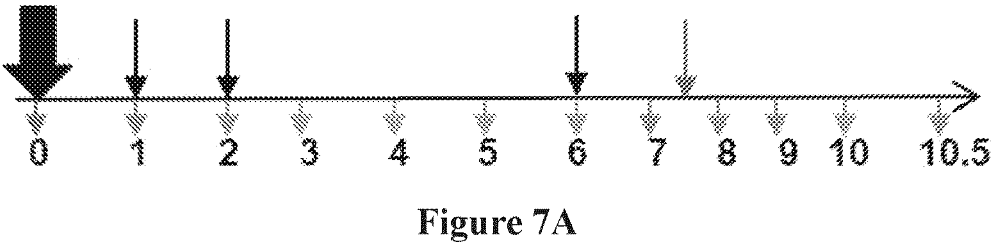
FIGS. 7A-7F show the effect of vaccine regime on tumor growth.
Figure 7B:
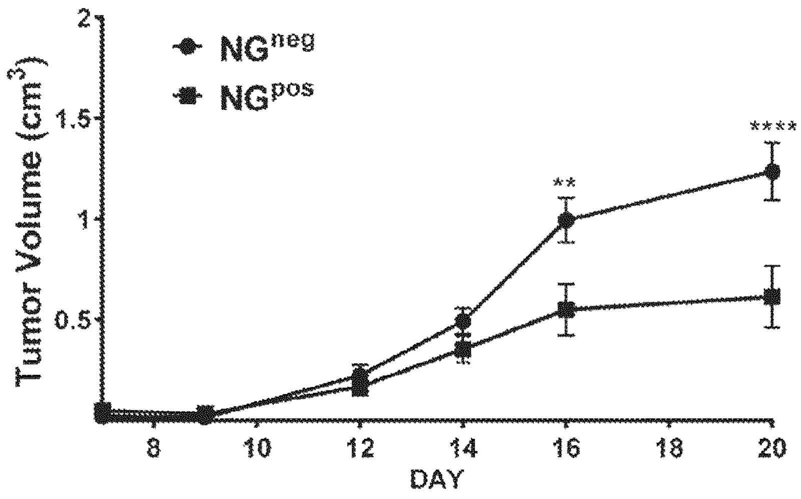
Figure 7C:
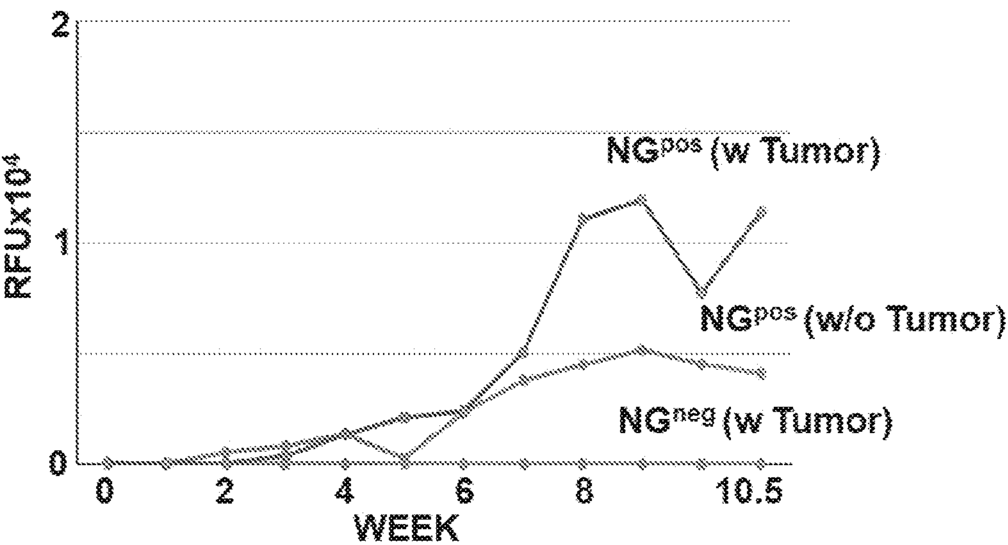
Figure 7D:
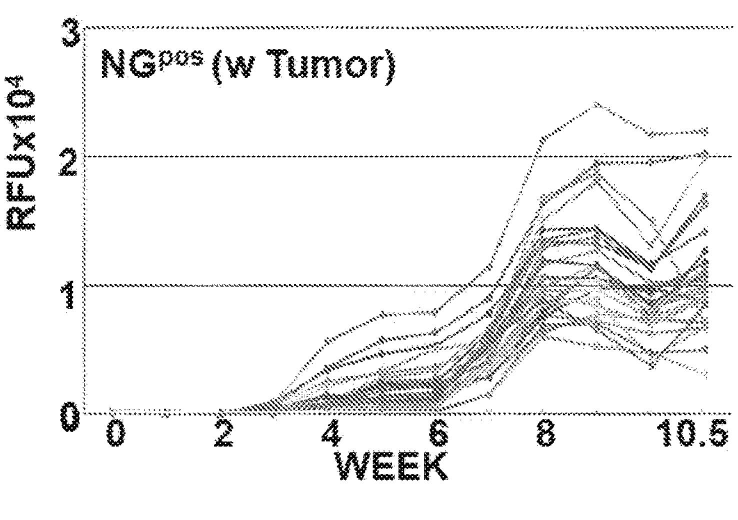
Figure 7E:
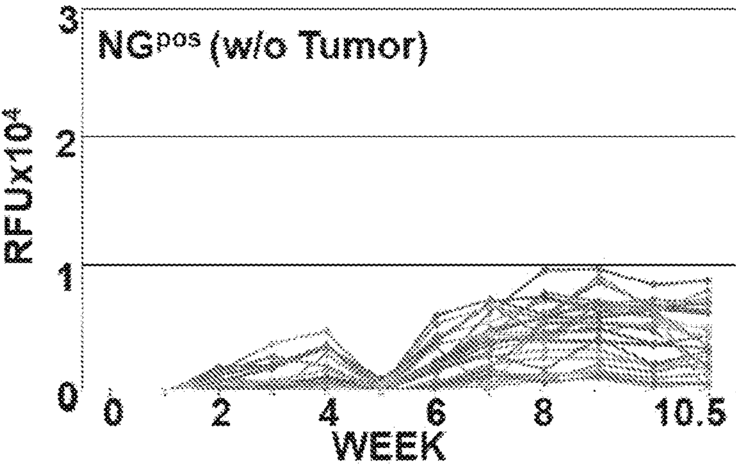
Figure 7F:
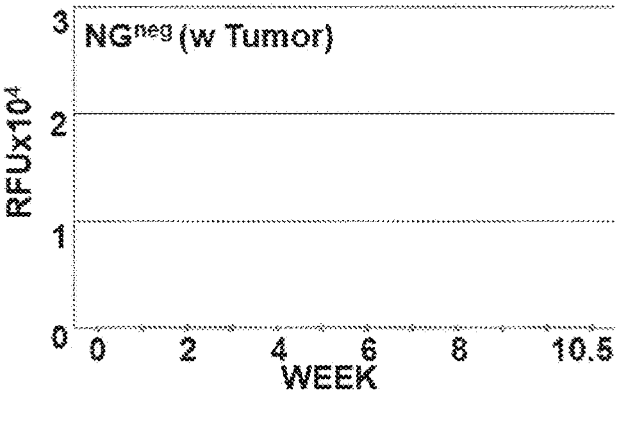
Figure 8:
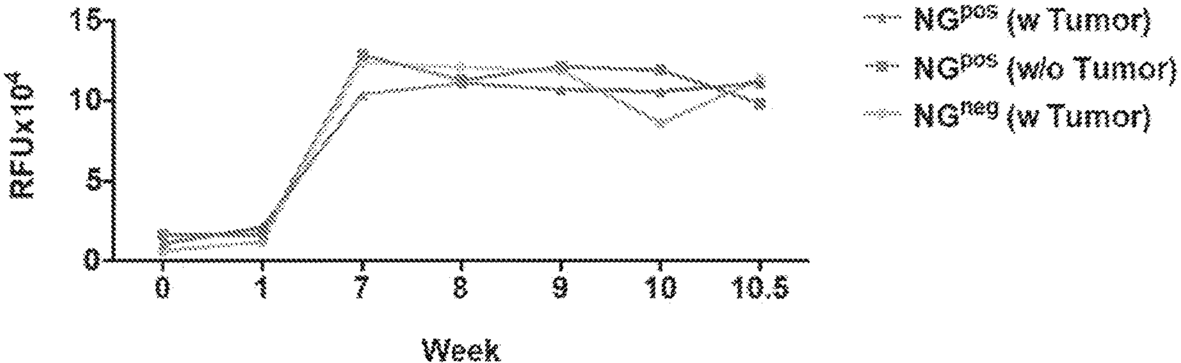
FIG. 8: IgG response against $NG^{pos}$ and $NG^{neg}$ in the vaccine and control treated mice (B1W regime).

Next, the therapeutic efficacy of the active vaccine regime and its effect on tumor growth were evaluated in vivo. Mice were immunized with $NG^{pos}$ or $NG^{neg}$ at the optimal B1W regime (weeks 0, 1, 2, 6; n=10 per group), then syngeneic Neu5Gc-positive tumors (MC-38) inoculated subcutaneously at week 7.5 (FIG. 7A, upper grey arrow), and tumor growth was monitored. In this case, tumor growth was dramatically inhibited in the vaccine treated group ($NG^{pos}$) compared to the control treatment ($NG^{neg}$) (FIG. 7B). Furthermore, glycan microarray analysis revealed that following $NG^{pos}$ vaccination, exposure to the inoculated Neu5Gc-positive tumors at week 7.5 mediated a dramatic enhancement in the average anti-Neu5Gc IgG response, compared to the group that had not been exposed to tumors (FIG. 7C). This reflected an increase in antibodies binding reactivity against all examined Neu5Gc-glycans (FIG. 7D and FIG. 7E), likely also representing an increase in the affinities of these antibodies. In contrast, the control $NG^{neg}$ treatment did not result in any serum response against Neu5Gc-glycans, even after tumors inoculation (FIG. 7F). Of note, all groups showed similar serum IgG responses to the NG-carrier, and tumor inoculation did not increase this response (FIG. 8). Together, these findings imply that the Neu5Gc-positive tumor cells themselves serve as secondary boosting agents, after priming of the immune system with $NG^{pos}$ vaccination, and these effects are specific to the immunogenic Neu5Gc carbohydrate antigen.

Example 4

Characterization of Purified Intra-Tumoral IgG

Figure 9:
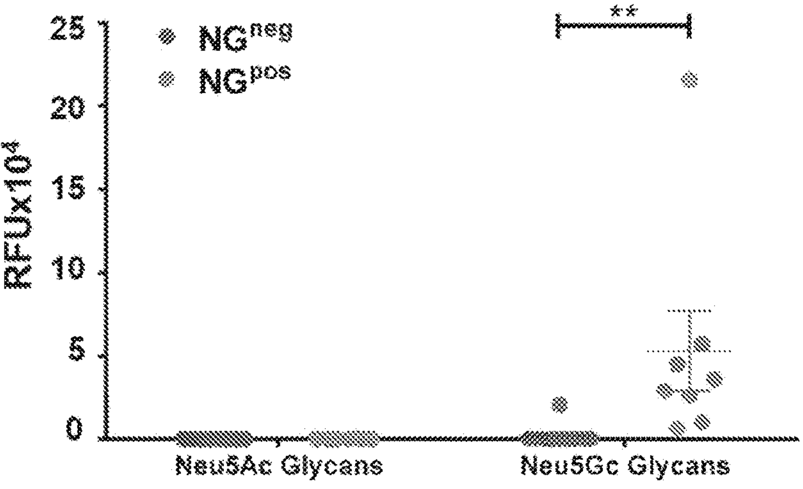
FIG. 9: Glycan microarray analysis of purified intratumoral IgGs of vaccine ($NG^{pos}$) or control ($NG^{neg}$) immunized mice.

Anti-Neu5Gc antibodies developed during the cancer vaccine treatment clearly play an important role in its therapeutic efficacy (FIGS. 7B and 7C). While $NG^{pos}$ vaccine treated mice showed tumor anti-Neu5Gc boosting effect during weeks 8-9, noticeably, they also displayed a transient depletion of serum anti-Neu5Gc IgG during week 10 (2.5 weeks after tumor inoculation), that was not observed in the non-tumor vaccine treated group (FIG. 7C). The drop in average response reflected a similar trend in the response to almost all individual Neu5Gc-glycans (FIGS. 7D-7E). To evaluate the hypothesis that these antibodies had migrated to the tumors, tumors were harvested, minced into suspension, then intra-tumoral antibodies purified by protein-A to capture IgG antibodies. Glycan microarray analysis of purified intra-tumoral IgGs revealed that all vaccine-treated mice ($NG^{pos}$; n=8) had a strong and highly-specific binding reactivity against all Neu5Gc-glycans but not Neu5Ac-glycans (FIG. 9), supporting migration of serum anti-Neu5Gc IgGs into the growing tumor mass. On the other hand, antibodies purified from tumors of control vaccination ($NG^{neg}$; n=10) showed mostly very low reactivity on the arrays (FIG. 9). Interestingly, a few mice in this control group had a very low but specific anti-Neu5Gc IgG response, likely mediated by the tumors that present foreign Neu5Gc-neoantigens. Notably, although MC-38 tumor cells express more Siaα2-3-linked than Siaα2-6-linked sialic acids, no distinct difference was detected in the epitopes recognized by the purified intra-tumoral IgG. Altogether, these results support the concept that anti-Neu5Gc IgG antibodies reach the tumor mass to mediate inhibition of tumor growth.

Example 5

Evaluating Heterogeneity in Vaccine Treatment

Figure 10A:
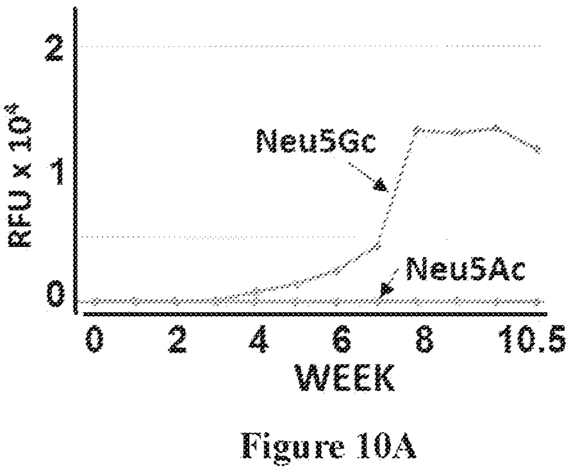
FIGS. 10A-10F are line graphs showing the kinetics of anti-Neu5Gc IgG response in vaccine treated mice, divided into three groups.
Figure 10B:
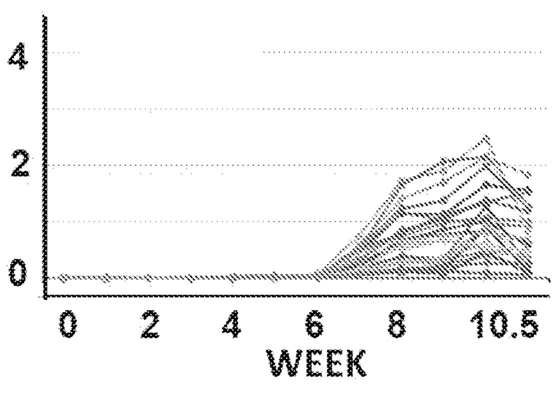
Figure 10C:
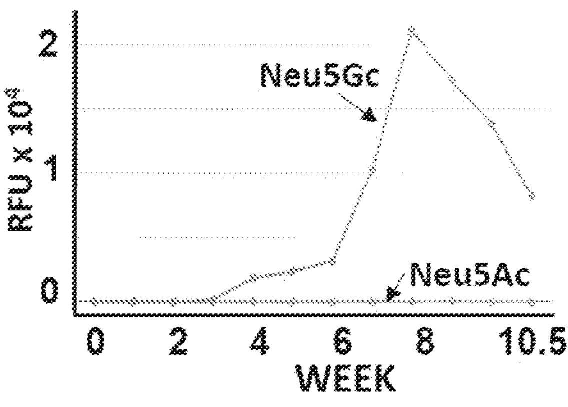
Figure 10D:
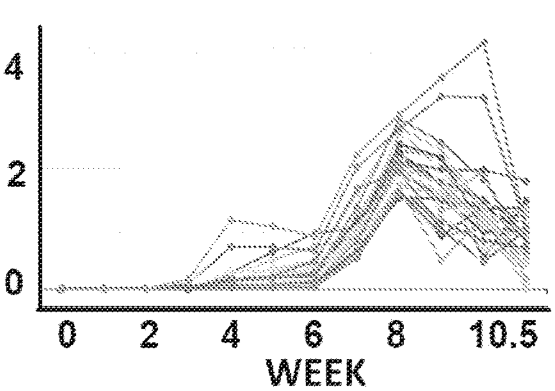
Figure 10E:
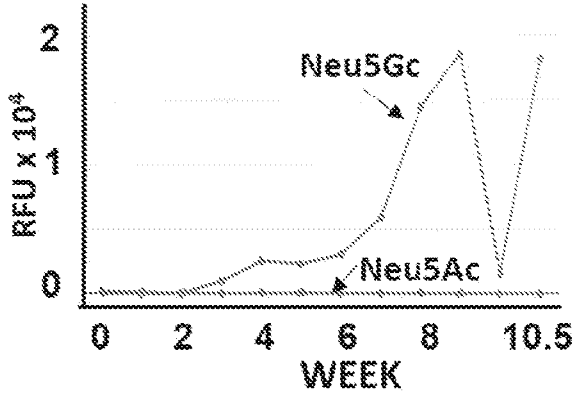
Figure 10F:
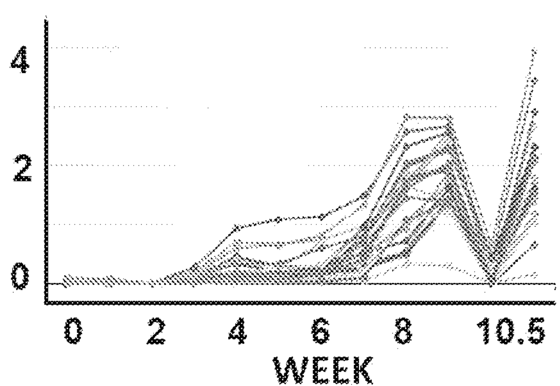
Figure 11A:
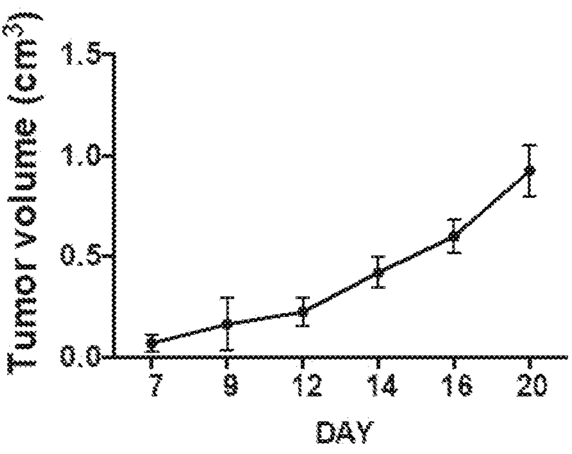
FIGS. 11A-11C are line graphs showing the average tumor growth kinetics in vaccine treated mice, divided into three groups: group 1 (FIG. 11A); group 2 (FIG. 11B); and group 3 (FIG. 11C).
Figure 11B:
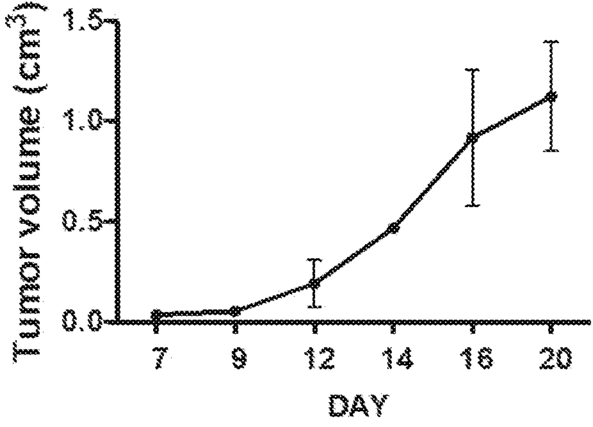
Figure 11C:
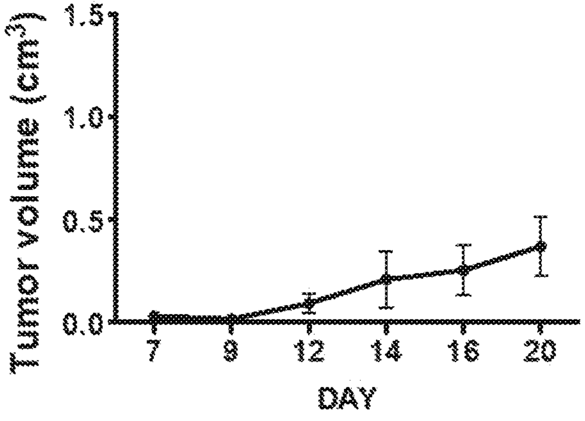

To evaluate heterogeneity in $NG^{pos}$ vaccination treatment, the kinetics of anti-Neu5Gc responses and tumor growth were monitored in each mouse individually. Analysis revealed three types of responses. Group 1 showed a late onset of response around week 6-7, with intermediate magnitude of response (FIG. 10A and FIG. 10B), and a low therapeutic effect on tumor (FIG. 11A). Group 2 showed a two-phase response initiating around weeks 3-4, followed by a secondary response immediately after the third boost vaccination on week 6, that had gradually decayed (FIG. 10C and FIG. 10D), with no therapeutic effect on tumors (FIG. 11B). By contrast, Group 3 showed a dramatic tumor inhibiting therapeutic effect (FIG. 11C), with a unique pattern of antibodies kinetics (FIG. 10E and FIG. 10F). In this group, there was a two-phase response as in group 2, however in addition there was an almost complete depletion of anti-Neu5Gc IgG from the serum on week 10, that was restored a few days later by week 10.5 (FIG. 10). This analysis clearly demonstrated that certain immune response kinetics, as developed in group 3, are more constructive in supporting the therapeutic effects mediated by the cancer vaccine. This suggest that in addition to the antibodies, the cellular arm of the immune system also plays an important role in the successful therapeutic effects, possibly involving CD8+ T cells mediated responses which have been show to contribute to other cancer vaccines.

Example 6

Combination Therapy of NG Vaccination with Immune Checkpoint Inhibitors

In vivo experiments are performed in order to examine the efficacy of combination therapy of the active cancer vaccine with checkpoint inhibitors. The experiment includes four groups of $Cmah^{-/-}$ mice (6-10 weeks old):

1. Control group: Immunization with $NG^{neg}$
2. $NG^{pos}$ monotherapy: Immunization with $NG^{pos}$
3. Checkpoint (C.P.) monotherapy: Immunization with anti-CTLA-4 and anti-PD1
4. Combined therapy: Immunization with $NG^{pos}$+C.P. antibodies Immunization is performed intraperitoneally (i.p.) on week 0,1,2 and 6. For the immunization, NG (either $NG^{pos}$ or $NG^{neg}$) at 2 mg/ml protein concentration are mixed (1:1) with FCA until emulsified. 200 µl (100 µg NG/mouse) are injected at week 0. At week 1, 2 and 6, three boosts injections are given, mixed 1:1 with FIA. On week 9, mice are inoculated subcutaneously with MC-38-GFP tumor cells ($0.5\times10^6$ cells/mouse in 150 µl DPBS). Immune checkpoint inhibitors antibodies (anti-CTLA-4 and anti-PD1) are injected i.p. on days 4, 8, 14, and 18 after tumor inoculation. During the experimental period, mice sera is sampled weekly and tumor growth is monitored by daily measurements using a digital caliper and tumor volume calculation. Sera samples are stored at −80° C. until analyzed by glycan microarray. On week 12, mice are sacrificed and then tumors are collected, weighed and analyzed for IgG intra-tumoral antibodies, RNA expression and FACS analysis of tumor/immune cells. FACS Analysis is used to decipher the immune cells populations that contribute to inhibition of tumor growth.

Antibodies in the blood samples (plasma) are analyzed by sialoglycan microarrays containing diverse sialoglycans and by FACS analysis of white blood cells. The analysis of antibodies in plasma is used for evaluation of anti-Neu5Gc response developed in the vaccine treated group and lack of response in the control vaccinated group.

Overall, preliminary results indicate that combining the active cancer vaccine with checkpoint inhibitors (group 4) provides better therapeutic outcomes than either of the therapies individually (groups 2 and 3), with higher inhibitory effect on tumor growth.

The project leading to this application has received funding from the European Research Council (ERC) under the European Union's Horizon 2020 research and innovation programme (grant agreement No 716220)

Although the present invention has been described herein above by way of preferred embodiments thereof, it can be modified, without departing from the spirit and nature of the subject invention as defined in the appended claims.

The invention claimed is:

1. An immunogenic composition comprising a plurality of membrane vesicles bearing N-glycolylneuraminic acid (Neu5Gc) glycoconjugates;

wherein the Neu5Gc glycoconjugates are exposed on the outer surface of the membrane vesicles;

wherein said membrane vesicles are cell ghosts derived from the outer plasma membrane of a porcine $Ggta1^{-/-}$ red blood cell expressing Neu5Gc; and wherein the membrane vesicles have an average hydrodynamic diameter in the submicron range.

2. The immunogenic composition according to claim 1, wherein the average hydrodynamic diameter of the membrane vesicles is within the range of 30-1000 nm.

3. The immunogenic composition according to claim 1, further comprising at least one additional tumor-associated antigen, wherein the at least one additional tumor-associated antigen is exposed on the outer surface of the membrane vesicle.

4. The immunogenic composition according to claim 1, further comprising an adjuvant approved for human use.

5. A vaccine comprising the immunogenic composition according to claim 1.

6. A method of stimulating an anti-cancer immune response in a subject, the method comprising administering the vaccine of claim 1 to the subject.

7. The method according to claim 6, wherein the cancer is Neu5Gc-positive.

8. The method according to claim 6, comprising repeated administrations.

9. The method according to claim 6, further comprising administering an additional immunotherapeutic drug to the subject.

10. The method according to claim 9, wherein the vaccine and the additional immunotherapeutic drug are administered substantially simultaneously, concurrently, alternately, successively or according to overlapping schedules.

11. The method according to claim 9, wherein the additional immunotherapeutic drug is an immune checkpoint inhibitor.

12. The method according to claim 11, wherein the immune checkpoint inhibitor is selected from PD-1 inhibitor, PD-L1 inhibitor and CTLA-4 inhibitor.

* * * * *